(12) United States Patent
Lanatta et al.

(10) Patent No.: US 11,317,059 B1
(45) Date of Patent: Apr. 26, 2022

(54) METHOD AND SYSTEM FOR MANAGING COMMUNICATIONS BETWEEN A VETERINARIAN AND A PET OWNER INCLUDING VIDEO COMMUNICATIONS

(71) Applicant: Boehringer Ingelheim Animal Health USA Inc., Duluth, GA (US)

(72) Inventors: Nicolas Lanatta, Buenos Aires (AR); Andrew Gillies, Dacula, GA (US)

(73) Assignee: Boehringer Ingelheim Animal Health USA Inc., Duluth, GA (US)

(*) Notice: Subject to any disclaimer, the term of this patent is extended or adjusted under 35 U.S.C. 154(b) by 0 days.

(21) Appl. No.: 16/827,805

(22) Filed: Mar. 24, 2020

Related U.S. Application Data

(60) Provisional application No. 62/823,531, filed on Mar. 25, 2019.

(51) Int. Cl.
| | |
|---|---|
| H04N 7/15 | (2006.01) |
| H04L 29/06 | (2006.01) |
| G16H 80/00 | (2018.01) |
| H04M 1/72439 | (2021.01) |
| H04L 65/403 | (2022.01) |
| H04L 65/1069 | (2022.01) |
| G06Q 10/02 | (2012.01) |
| G06Q 10/10 | (2012.01) |
| G06Q 20/40 | (2012.01) |
| G16H 15/00 | (2018.01) |
| G16H 10/60 | (2018.01) |
| G06Q 30/02 | (2012.01) |
| G06Q 20/10 | (2012.01) |

(52) U.S. Cl.
CPC ............... *H04N 7/15* (2013.01); *G06Q 10/02* (2013.01); *G06Q 10/1095* (2013.01); *G06Q 20/102* (2013.01); *G06Q 20/4037* (2013.01); *G06Q 30/0234* (2013.01); *G16H 10/60* (2018.01); *G16H 15/00* (2018.01); *G16H 80/00* (2018.01); *H04L 65/1069* (2013.01); *H04L 65/403* (2013.01); *H04M 1/72439* (2021.01)

(58) Field of Classification Search
USPC .......................................... 348/14.08, 14.02
See application file for complete search history.

(56) References Cited

U.S. PATENT DOCUMENTS

| | | |
|---|---|---|
| 6,678,613 B2 | 1/2004 | Andrews et al. |
| 6,947,411 B2 | 9/2005 | Parker et al. |
| 6,988,075 B1 | 1/2006 | Hacker |

(Continued)

*Primary Examiner* — Maria El-Zoobi

(57) ABSTRACT

A method and system for managing communications between a veterinarian (vet) and a pet owner including video communications may integrate pet medical records access along with allowing a vet to view as well as annotate pet medical records during a video consultation with the pet owner. Either the vet or the pet owner may set up a video conference between each other. The method and system may establish a video conference in which a vet may access the video conference with a desktop computer while the pet owner accesses the video conference a portable computing device (PCD). A video conference may be established by the pet owner, usually, after payment information from a financial card is supplied to the system. The method and system provides a chat functionality, which can be initiated by the pet owner or the vet, and allows both parties to send/receive messages and/or images.

10 Claims, 29 Drawing Sheets

(56) References Cited

U.S. PATENT DOCUMENTS

| | | |
|---|---|---|
| 7,039,878 B2 | 5/2006 | Auer et al. |
| 7,380,707 B1 | 6/2008 | Fredman |
| 7,412,396 B1 | 8/2008 | Haq |
| 7,613,620 B2 | 11/2009 | Salwan |
| 7,743,979 B2 | 6/2010 | Fredman |
| 7,860,725 B2 | 12/2010 | Gopinathan et al. |
| 7,912,733 B2 | 3/2011 | Clements et al. |
| 7,929,465 B2 | 4/2011 | Parker et al. |
| 8,015,049 B1 | 9/2011 | Tam et al. |
| 8,321,284 B2 | 11/2012 | Clements et al. |
| 8,390,694 B2 | 3/2013 | Ryan et al. |
| 8,423,288 B2 | 4/2013 | Stahl et al. |
| 8,589,177 B2 | 11/2013 | Haq |
| 8,660,790 B2 | 2/2014 | Stahl et al. |
| 9,207,084 B2 | 12/2015 | Stahl et al. |
| 9,251,314 B2 | 2/2016 | Kanagala |
| 9,264,649 B2 | 2/2016 | Ryan et al. |
| 9,280,888 B2 | 3/2016 | Ramsdell et al. |
| 9,491,206 B2 | 11/2016 | Nur et al. |
| 9,619,787 B2 | 4/2017 | Stahl et al. |
| 2002/0004727 A1 | 1/2002 | Knaus et al. |
| 2003/0204474 A1* | 10/2003 | Capek ............... G06Q 20/382 705/64 |
| 2005/0049898 A1 | 3/2005 | Hirakawa |
| 2008/0018454 A1 | 1/2008 | Chan et al. |
| 2008/0077431 A1 | 3/2008 | Calder et al. |
| 2008/0201429 A1 | 8/2008 | Barbell et al. |
| 2008/0275311 A1* | 11/2008 | Haq ..................... G16H 50/20 600/300 |
| 2010/0030580 A1 | 2/2010 | Salwan |
| 2010/0257047 A1* | 10/2010 | Foodman ............. G06Q 30/04 705/14.26 |
| 2012/0130742 A1 | 5/2012 | Church et al. |
| 2013/0060576 A1 | 3/2013 | Hamm et al. |
| 2014/0040099 A1* | 2/2014 | Keitz ................... G06Q 20/02 705/37 |
| 2014/0052463 A1 | 2/2014 | Cashman et al. |
| 2014/0108029 A1 | 4/2014 | Kim |
| 2014/0229547 A1* | 8/2014 | Justin ................. H04L 65/4023 709/204 |
| 2014/0267299 A1 | 9/2014 | Couse |
| 2015/0035959 A1* | 2/2015 | Amble ................... G11B 27/11 348/74 |
| 2015/0278453 A1* | 10/2015 | Joao ..................... G06F 19/00 705/3 |
| 2016/0224763 A1 | 8/2016 | Ethington et al. |
| 2016/0300031 A1 | 10/2016 | Salwan |
| 2017/0242963 A1 | 8/2017 | Cohen et al. |
| 2018/0322947 A1 | 11/2018 | Potts et al. |
| 2019/0096534 A1* | 3/2019 | Joao ..................... G16H 15/00 |
| 2019/0320900 A1* | 10/2019 | Majmudar ........... G16H 20/30 |

* cited by examiner

WHAT'S YOUR E-MAIL?

Make sure you use the email address your Vet-Practice Management Software (V-PMS) has on file. Learn why.

Email: VET@BUTLERCREEKANIMAL.COM (CONTINUE)

IS THIS YOUR CLINIC?

Butler Creek Animal Hospital
7278 N. Milwaukee Ave.
Niles, IL 160714

Not your clinic?

CONFIRM

FIG. 1D

SELECT A PET OWNER THAT YOU WANT TO INVITE TO CREATE AN ACCOUNT:

136

Search

1. Ashburton, Jane
2. Byron, Michelle A.
3. Casey, Samuel J.

Click on the hypertext link in the Pet Owner Name to select a Pet Owner for receiving the invitation code.

FIG. 1E

METHOD AND SYSTEM FOR MANAGING COMMUNICATIONS BETWEEN A VETERINARIAN AND A PET OWNER INCLUDING VIDEO COMMUNICATIONS

BACKGROUND

Currently, when a pet owner of a companion animal, such as a dog, cat or bird, needs to see a veterinarian (vet), the pet owner usually must schedule a standard appointment in which the pet owner travels to seethe vet at the vet's brick-and-mortar clinic. In addition to the journey to the vet clinic being burdensome on the pet owner, the pet owner must also transport the companion animal to the vet clinic which adds to the complexity of seeing the vet with the companion animal. It is well known that companion animals traveling in a vehicle can disrupt a respective companion animal's behavior and/or mood.

Another problem in the art occurs when vets sell products to pet owners. Often, vets provide incentives for pet owners to purchase products directly from the vets to encourage and/or foster relationships among the pet owners. Exemplary incentives for purchasing products directly from vets includes coupons and/or rebates. However, paper based coupons and/or rebates are often too burdensome to track by pet owners. The time and challenge to receive value from submitting paper-based rebates through standard postal, paper mailing systems is quite excessive and often prohibitive for the ordinary pet owner.

Therefore, what is needed in the art is a system and method for managing communications between a veterinarian and a pet owner including video communications such that the video communications may eliminate a need for the pet owner to visit the brick-and-mortar clinic of the veterinarian. Another need exists in the art to eliminate paper-based coupons and rebates, such that value can be received from the pet owner electronically instead of relying on paper-based communications to secure the value.

SUMMARY OF THE INVENTION

A method and system for managing communications between a veterinarian (vet) and a pet owner including video communications may integrate pet medical records access along with allowing a vet to view as well as annotate pet medical records during a video consultation with the pet owner. Either the vet or the pet owner may set up a video conference between each other. The method and system may establish a video conference in which a vet may access the video conference with a desktop computer while the pet owner accesses the video conference a portable computing device (PCD) [i.e. a mobile phone, a tablet PC, or other hand-held computing device].

A video conference may be established by the pet owner, usually, after payment information from a financial card [credit card, debit card, reward card, etc.] or other payment provider is supplied to the system which verifies that the information is accurate. The method and system usually does not charge the pet owner for the video conference scheduled with the vet until the video conference is completed between the vet and the pet owner.

A video conference may be established by the vet and usually at no cost to the pet owner when the vet initiates a need for a video conference. The vet may immediately reach the pet owner by a video conference call by initiating a call from the desktop application of the system which is available to the vet.

The method and system also provide a platform wherein both the vet and pet owner may exchange text based messages as well as images such as photographs captured with a portable computing device, like a mobile phone. The vet may send messages from a desktop computer while the pet owner may send messages from a hand-held portable computing device, such as a mobile phone.

The method and system may also provide the vet as well as the pet owner with access to the pet medical records originated by the vet for care of the companion animal. The pet owner may be provided with view only access of the pet medical records on the portable computing device while the vet may be provide with full access, that includes, viewing, editing, and annotating pet medical records for a companion animal.

The method and system may also integrate the ability to schedule a video conference with the ability to electronically redeem coupons and/or rebates issued electronically from the vet to the pet owner. That is, when a pet owner purchases pet products and/or services from a vet, the vet may issue electronic coupons for new products and/or services as well as electronic rebates for products and/or services which were purchased by the pet owner.

Using the portable computing device (PCD), a pet owner may see past purchased products and/or services with the system as well as rebates or coupons associated with these past purchased products. For rebates, the pet owner may select a rebate on a display screen of the portable computing device for redemption and the system may automatically upload the rebate once selected by the pet owner.

The pet owner may then be sent a message from the system once the rebate is approved for redemption and then the pet owner with the portable computing device may redeem value from the rebate associated with the past purchased product from the vet. The pet owner may select with the portable computing device how this value may be received: in the form of currency added to a financial card [credit card, debit card, stored value card, etc.], currency added to a financial account [i.e. a bank account etc.], or in the form of loyalty points associated with the account tracked by the method and system.

With the method and system, a vet clinic may utilize its existing off-the-shelf, third party practice management systems (PMS) for creating, storing, and appending pet medical records for companion animals. The method and system may access the existing practice management system and keep copies of such records that were originated by the existing practice management system. The method and system may supply annotated records and upload these annotated records to the existing practice management system.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

In the drawings, like reference numerals refer to like parts throughout the various views unless otherwise indicated. For reference numerals with letter character designations such as "102A" or "102B", the letter character designations may differentiate two like parts or elements present in the same figure. Letter character designations for reference numerals may be omitted when it is intended that a reference numeral to encompass all parts having the same reference numeral in all figures.

FIG. 1C illustrates an exemplary user interface (UI) that may be displayed on the vet desktop device to receive account information related to a third party vet practice management system (V-PMS);

FIG. 1D illustrates an exemplary user interface (UI) that may be displayed on the vet desktop device to confirm V-PMS account information;

FIG. 1F illustrates an exemplary user interface (UI) that may be displayed on the pet owner mobile device for setting up an account with the integration server 201C by using the invitation code;

FIG. 1O illustrates a user interface (UI) that may be displayed on the vet desktop device for displaying calendar data, including information about past, present, and future video calls scheduled with a vet desktop device;

FIG. 1Y-2 illustrates a user interface (UI) that may be displayed on the pet owner mobile device which lists one or more payment options for the value of a redeemed rebate that may be selected by the pet owner mobile device;

DETAILED DESCRIPTION OF EXEMPLARY EMBODIMENTS

The term "exemplary" is used herein to mean "serving as an example, instance, or illustration." Any aspect described herein as "exemplary" is not necessarily to be construed as preferred or advantageous over other aspects.

In this description, the term "application" may also include files having executable content, such as: object code, scripts, byte code, markup language files, and patches. In addition, an "application" referred to herein, may also include files that are not executable in nature, such as documents that may need to be opened or other data files that need to be accessed.

The term "content" may also include files having executable content, such as: object code, scripts, byte code, markup language files, and patches. In addition, "content" referred to herein, may also include files that are not executable in nature, such as documents that may need to be opened or other data files that need to be accessed.

As used in this description, the terms "component," "database," "module," "system," "engine", and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer.

By way of illustration, both an application running on a computing device and the computing device may be a component. One or more components may reside within a process and/or thread of execution, and a component may be localized on one computer and/or distributed between two or more computers. In addition, these components may execute from various computer readable media having various data structures stored thereon.

The components may communicate by way of local and/or remote processes such as in accordance with a signal having one or more data packets (e.g., data from one component interacting with another component in a local system, distributed system, and/or across a network such as the Internet with other systems by way of the signal).

Figure 1A:
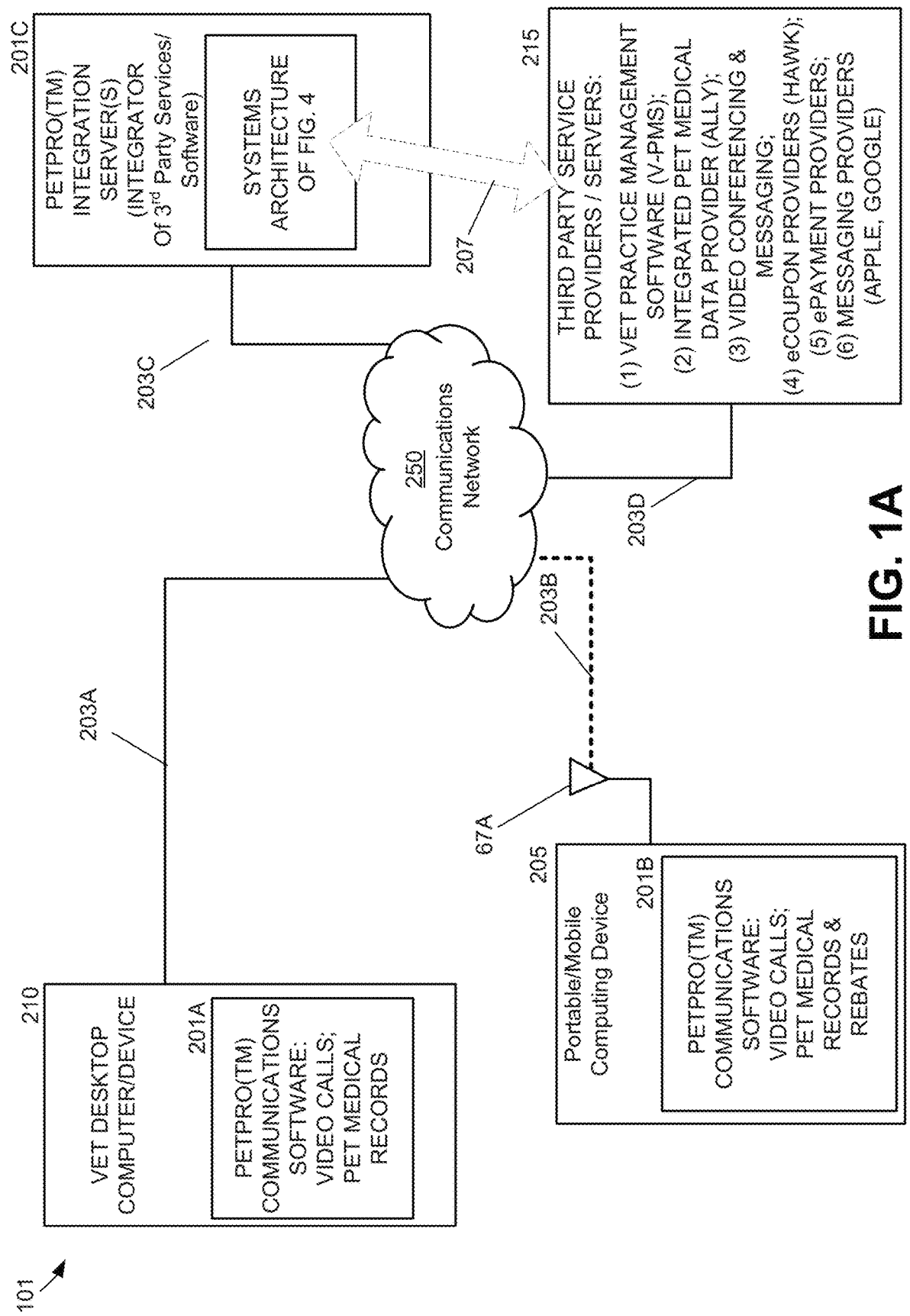
FIG. 1A illustrates an exemplary system for managing communications between a veterinarian (via a vet desktop computer) and a pet owner (via a portable computing device, i.e. a mobile phone/tablet) including video communications.
Figure 1B:
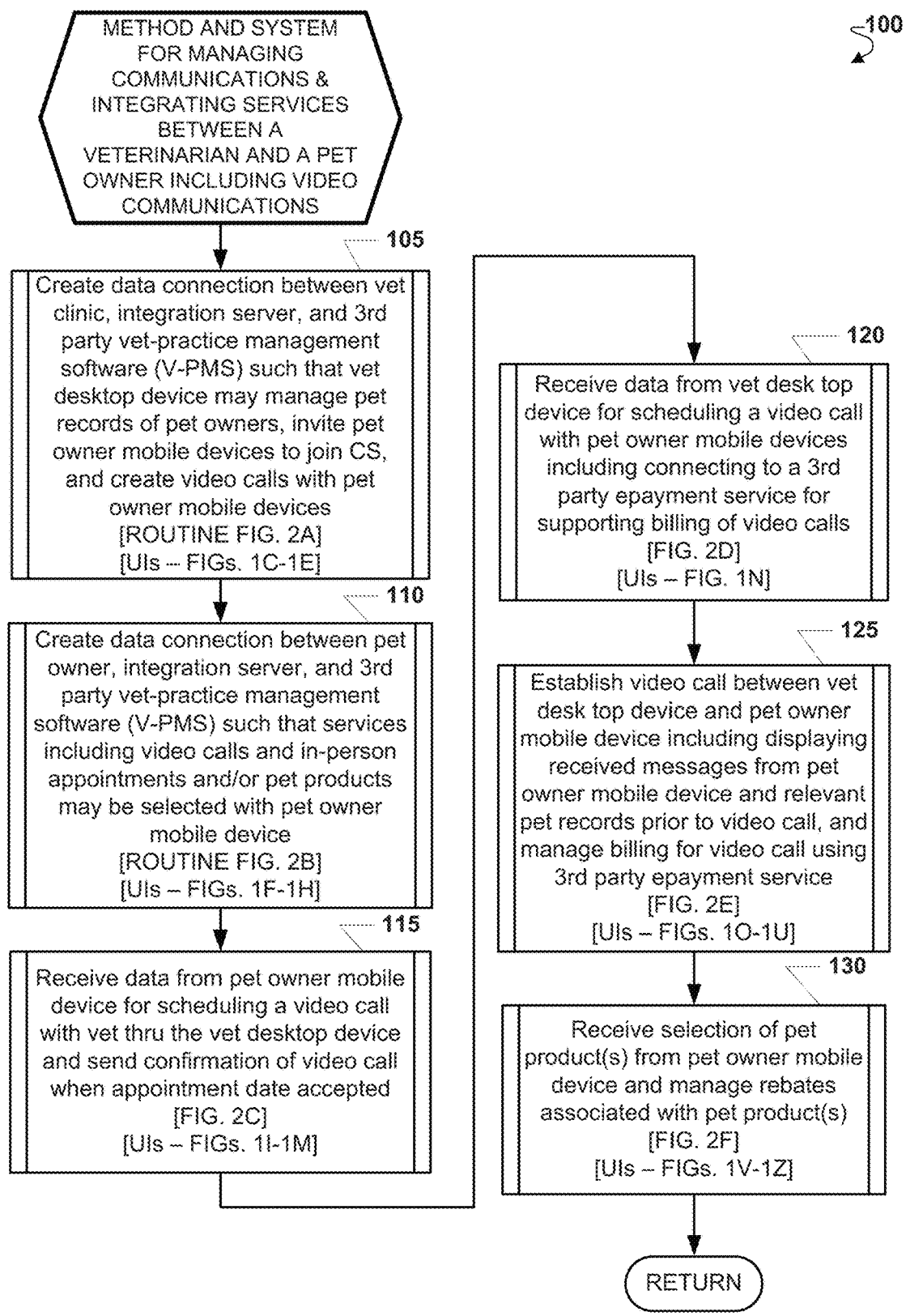
FIG. 1B illustrates flow chart of a method for managing communications between a veterinarian (vet) desktop device and a pet owner mobile device including video communications that integrates pet medical records access along with allowing a vet desktop device to view as well as annotate pet medical records during a video consultation with the pet owner mobile device.
Figure 1G:
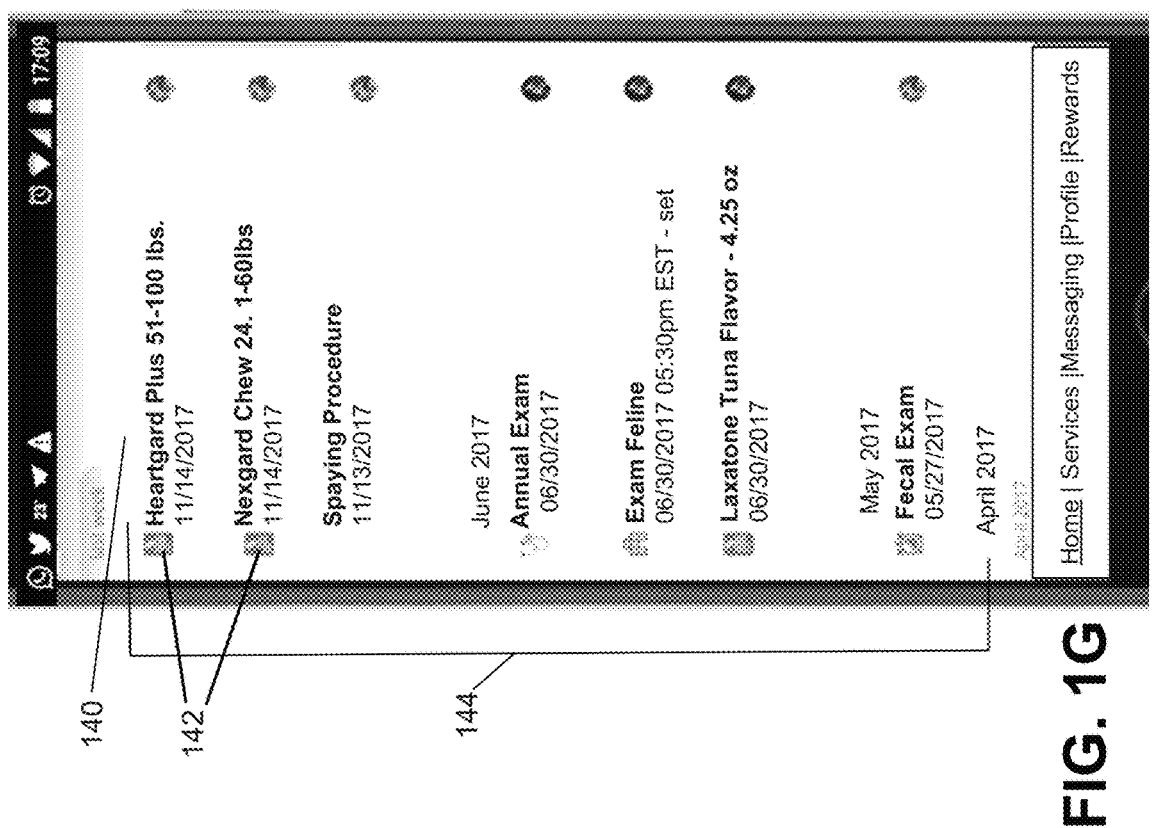
FIG. 1G illustrates a user interface (UI) that may be displayed on the pet owner mobile device for listing pet records and suggested products and/or services available from the vet clinic.

Referring now to the drawings, wherein the visuals are for purposes of illustrating certain exemplary embodiments of the present disclosure only, and not for purposes of limiting the same, FIGS. 1A-1B provide a system diagram and a high-level flow chart for the method performed by one or more of the system elements illustrated in FIG. 1A. FIGS. 1C-1Z illustrate exemplary embodiments of screen displays for portable computing devices (PCDs) as well desktop-based computing devices, such as a desktop computer.

Usually, pet owners will use PCDs while veterinarians (vets) will use desktop computers. However, it is possible for either user (pet owner or vet) to use other devices where the pet owner could use a desktop computer and a vet could use a PCD without departing from this disclosure. Each PCD may comprise at least one of a cellular telephone, a smartphone, a portable digital assistant (PDA), a portable game console, a navigation device, and a tablet computer.

The animals described in this disclosure may comprise any type of animal. Exemplary animals include, but are not limited to, dogs, fox, cats, ferrets, raccoons, wildcats, calves, cows, piglets, sheep, pigs, hogs, boars, horses, oxen, zebras, camels, dromedaries, lamas, ostriches, deer, elks, moose, monkeys, chicken, hens, turkeys, geese, and various species of birds; tuna, dolphins, sharks, and various species of fish; lions, panthers, puma, etc. Production animals as well as companion animals may be well suited for this system. Production animals usually include, but are not limited to, calves, cows, piglets, sheep, pigs, hogs, horses, chickens, hens, turkeys, and geese. Meanwhile, companion animals usually include, but are not limited to, dogs and cats.

Referring now to FIG. 1A, this figure illustrates an exemplary system 101 for managing communications between a veterinarian (vet desktop computer 210) and a pet owner (portable computing device 205) including video communications. The system 101 may integrate pet medical records access along with allowing a vet (via vet desktop computer 210) to view as well as annotate pet medical records during a video consultation with the pet owner.

The vet desktop computer 210 may run/execute a PetPro™ brand communications software 201A. Alternatively, the communication software 201A could be accessed by a web browser which communicates with the PetPro™ brand integration servers 201C. The integration server 201C "integrates"/combines several different off-the-shelf services, such as video services and rebate services, into a unique software as a service (SaaS) model.

The portable computing device (PCD) 205 of the pet owner may also run a local application/module comprising a PetPro™ communications software module 201B designed for portable computing device (PCD) operating systems (i.e. OS for mobile phones like Apple™ IOS, and Android™ OS). Both the desktop communications software module 201A and the PCD communications software module 201B communicate with the integration server 201C over a communications network 250 via communication links 203.

The communications network 250 may comprise the worldwide web (WW) or the Internet, a wide area network ("WAN"), the plain-old-telephone-system ("POTS), a local area network ("LAN"), the Internet, or any combination of these and other types of networks. The communication links 203 may be wired or wireless or any combination thereof.

For the vet desktop computer 210, the communications software module 201A may provide support for video calls with the PCD 205 as well as allowing the vet to read, write, and annotate pet medical records. Meanwhile, the communications software module 201B for the PCD 205, may provide read only access to pet medical records for the pet owner as well as supporting video conference calls with the desktop computer 210. Additionally, the communications software module 201B for the PCD 205 may also support processing and redemption of electronic rebates associated with products and/or services sold by the vet.

The integration server(s) 201C may integrate several different third party, off-the-shelf service providers 215 to support the functions and features of the software module 201A, 201B running on the desktop computer 210 and PCD 205. Dashed arrow 207 represents a virtual connection and/or integration with these third party service providers 215. The third party service providers 215 include, but are not limited to, at least vet practice management software/services ("V-PMS") for handling pet medical records of a vet clinic; a third party integrated pet medical data provider (such as Ally™ brand data provider known as of this writing); video conferencing providers (such as OpenTok™ conferencing provider known as of this writing); eCoupon providers (such as HAWK™ brand eCoupon services known as of this writing); ePayment Providers (such as STRIPE™ brand of ePayment services known as of this writing); and third party messaging providers (such as APPLE™ and GOOGLE™ brand message providers known as of this writing).

The PetPro™ brand integration server(s) 201C may follow the data system architecture of FIG. 3 (described below) and the one or more servers 201C may be programmed as special purpose computers programmed to perform the disclosed algorithms (shown in flow chart forms) illustrated in FIGS. 1B-2E. The integration server(s) 201C essentially integrate the services/functions of several off-the-shelf, third party providers 215 by using various different application programming interfaces (APIs) to communicate with these third party providers as will be described below.

Referring now to FIG. 1B, this figure illustrates a flow chart of a method 100 for managing communications between a veterinarian (vet) desktop device 210 and a pet owner mobile device 205 including video communications that integrates pet medical records access along with allowing a vet desktop device 210 to view as well as annotate pet medical records during a video consultation with the pet owner mobile device 205. In FIG. 1B, each step/function block illustrated is a high-level routine. That is, each step/function block of FIG. 1B generally corresponds to sub-methods or subroutines which have several steps executed by the special purpose computer/server 201C and that are further illustrated and explained in FIGS. 2A-2E.

Routine 105 is the first step of method 100 in which the integration server 201C may create a data connection between a vet clinic desktop device 210, the integration server (CS) 201C, and 3rd party vet-practice management software (V-PMS) 347 (See FIG. 3) such that vet desktop device 210 may manage pet records of pet owners, invite pet owner mobile devices communicate directly with the CS 201C, and create video calls with pet owner mobile devices 205. Routine 105 comprises the several steps shown FIG. 2A described in more detail below. Routine 105 also generally corresponds to the user interfaces (UI's) illustrated in FIGS. 1C-1E also described in further detail below.

Routine 105 generally provides a vet desktop device 210 with access to the V-PMS 347 so that the vet desktop device 210 may access pet records before a video call and during a video call. This access may include displaying (read) existing data, changing data, and adding new data to each pet medical record. During routine 105, the vet desktop device 210 may send messages via the integration server 201C to invite a pet owner mobile device 205 to create an account with the integration server 201C. Specifically, the message sent by the vet desktop device 210 via the integration server 201C may comprise an alpha-numeric code. This alpha-numeric code allows the pet owner mobile device 205 to activate the communication software 201B that may be downloaded and executed by the pet owner mobile device 205 as illustrated in FIG. 1A.

Next, in routine 110, a data connection is created by the integration server 201C among the integration server 201C, the pet owner mobile device 205, and the V-PMS 347 such that services including, but not limited to, video calls and in-person appointments and/or pet products may be selected with the pet owner mobile device 205. The details of routine 110 are illustrated in FIG. 2B and described below. The steps of routine 110 generally correspond with the user interfaces (UIs) of FIGS. 1F-1H which are also described in detail below.

During and after this routine 110 is executed by the pet owner mobile device 205, the pet owner mobile device 205 may have access to the V-PMS 347. This means that the pet owner mobile device 205 may be able to search and display pet records. However, usually, the pet owner will not be granted access to add or change any of the pet records. Also, during and after this routine 110, the integration server 201C may identify available treatments and/or pet products based on the data associated with a particular pet record.

For example, based on the current month (i.e. springtime associated with warmer weather and development of parasites like fleas and/or ticks) or based on when a pet may have had its last treatment, the integration server 201C could recommend a parasite treatment (i.e. flea/tick soap/bath service) for the companion animal which is the subject of the pet record. Other services products and/or services are possible and are included within the scope of this disclosure. This service may be displayed on the pet owner mobile device 205 and it may be available for selection by the pet owner on the mobile device 205.

During or after routine 110 is executed, the pet owner mobile device 205 may be able to schedule/create video calls with the vet desktop device 210. Further details of scheduling and creating video calls with the pet mobile device 205 will be described below.

Subsequently, in routine 115, the integration server 201C may receive data from the pet owner mobile device 205 for scheduling a video call with a vet through the vet desktop device 210. The integration server 201 may also send a confirmation of the video call to the pet owner mobile device 205 when the video call appointment date is accepted by the vet desktop device 210. Further details of this routine are illustrated in FIG. 2C. This routine 115 generally corresponds to the user interfaces (UIs) presented in FIGS. 1C-1M also described in further detail below.

During and/or after routine 115, the pet owner mobile device 205 may provide payment information to support video calls such that a pet owner's credit card and/or bank account is charged for a video call with a vet once the video call is ended. The pet owner mobile device 205 may provide this payment information that is stored in a third party ePayment service account as will be described below. During and/or after this routine 115, the pet owner mobile device may also send text messages to the desktop device 210, which may include images and/or video as described in detail below.

After routine 115, in routine 120 the integration server 201C may receive data from the vet desktop device 210 for scheduling a video call and/or initiating a video call with the pet owner mobile device 205. During routine 120, the integration server 201C may also receive data from the vet desktop device 210 for connecting to a third party ePayment service for managing the billing of video calls with pet owner mobile devices 205. Further details for routine 120 are illustrated in FIG. 2D. Routine 120 generally corresponds to the user interface (UIs) of FIG. 1N described in further detail below.

In routine 120, the integration server 201C may further receive time increments and the price per time increments in which a vet would like to bill video calls to a pet owner mobile device 205. The integration server 201C may store the time increments and price per increments in memory.

It is noted that routine 120 may occur before routine 115 and/or vice-versa. That is, the vet desktop device 210 may setup video call capability before the pet owner mobile device 205, or vice-versa. Also, these routines 115, 120 may also be performed in parallel as understood by one of ordinary skill in the art.

Next, in routine 125, the integration server 201C may establish a video call between the vet desktop device 210 and the pet owner mobile device 205, including displaying received messages from the pet owner mobile device 205 and relevant pet records prior to and/or during the video call for the vet desktop device 210. During routine 125, the integration server 201C may manage the billing for the video call using a third party ePayment service.

Figure 1P:
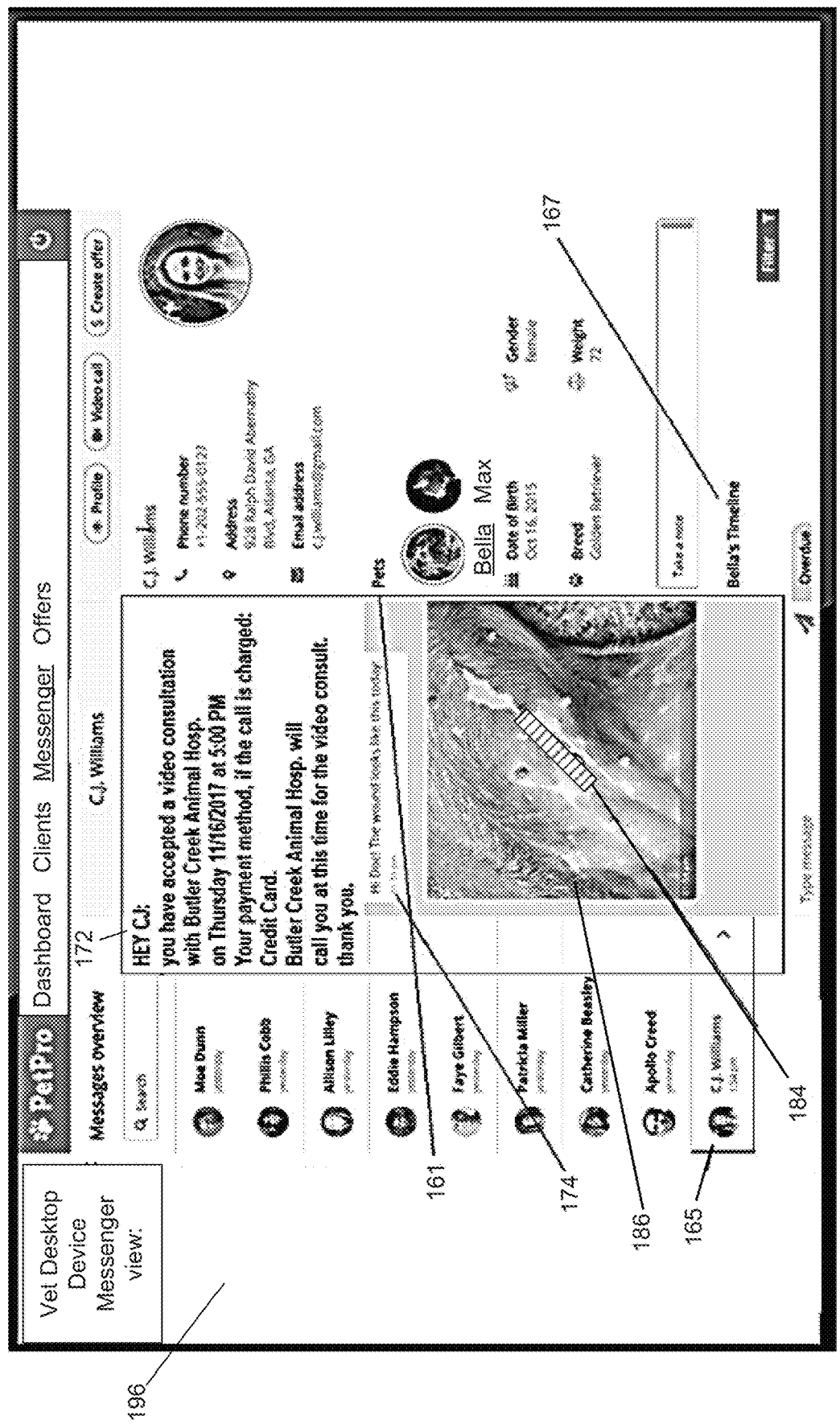
FIG. 1P illustrates a user interface (UI) that may be displayed on the vet desktop device for displaying messages received from pet owner mobile devices and for review by a vet prior to a video call.
Figure 1Q:
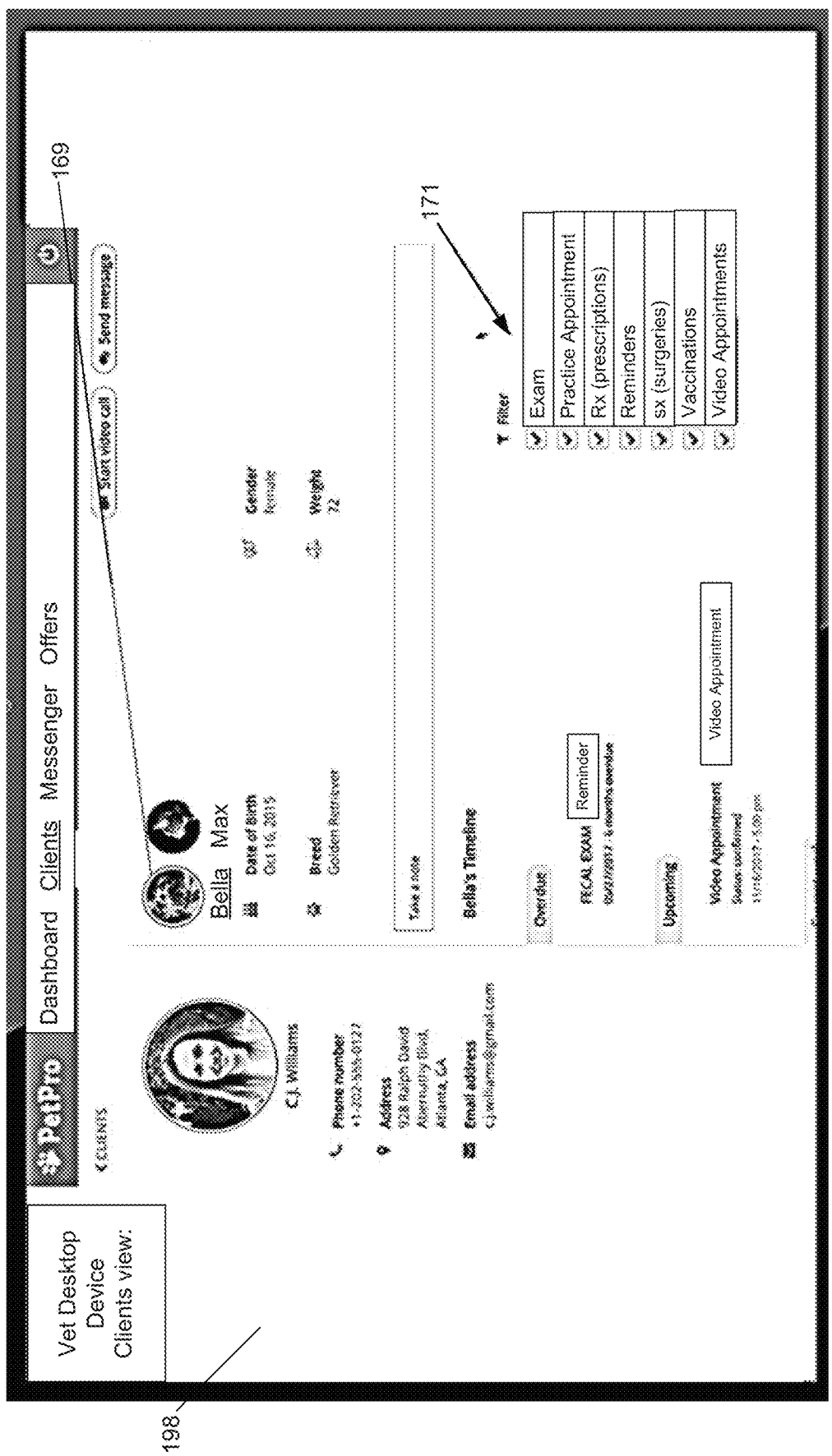
FIG. 1Q illustrates a user interface (UI) that may be displayed on the vet desktop device for reviewing pet medical records in more detail.
Figure 1R:
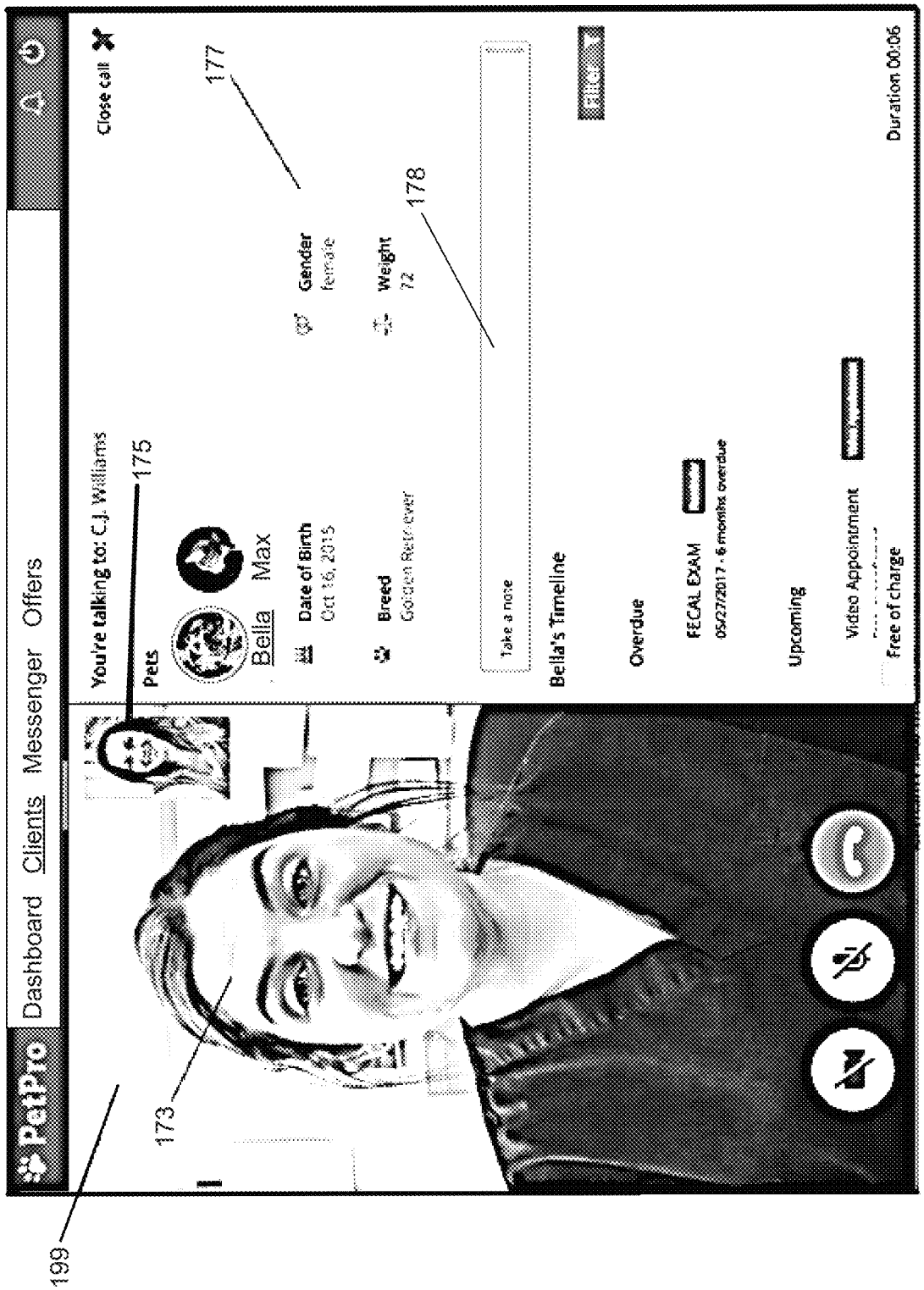
FIG. 1R illustrates a user interface (UI) that may be displayed on the vet desktop device and that allows a vet to initiate a video call with a pet mobile device being operated by a pet owner.
Figure 1S:
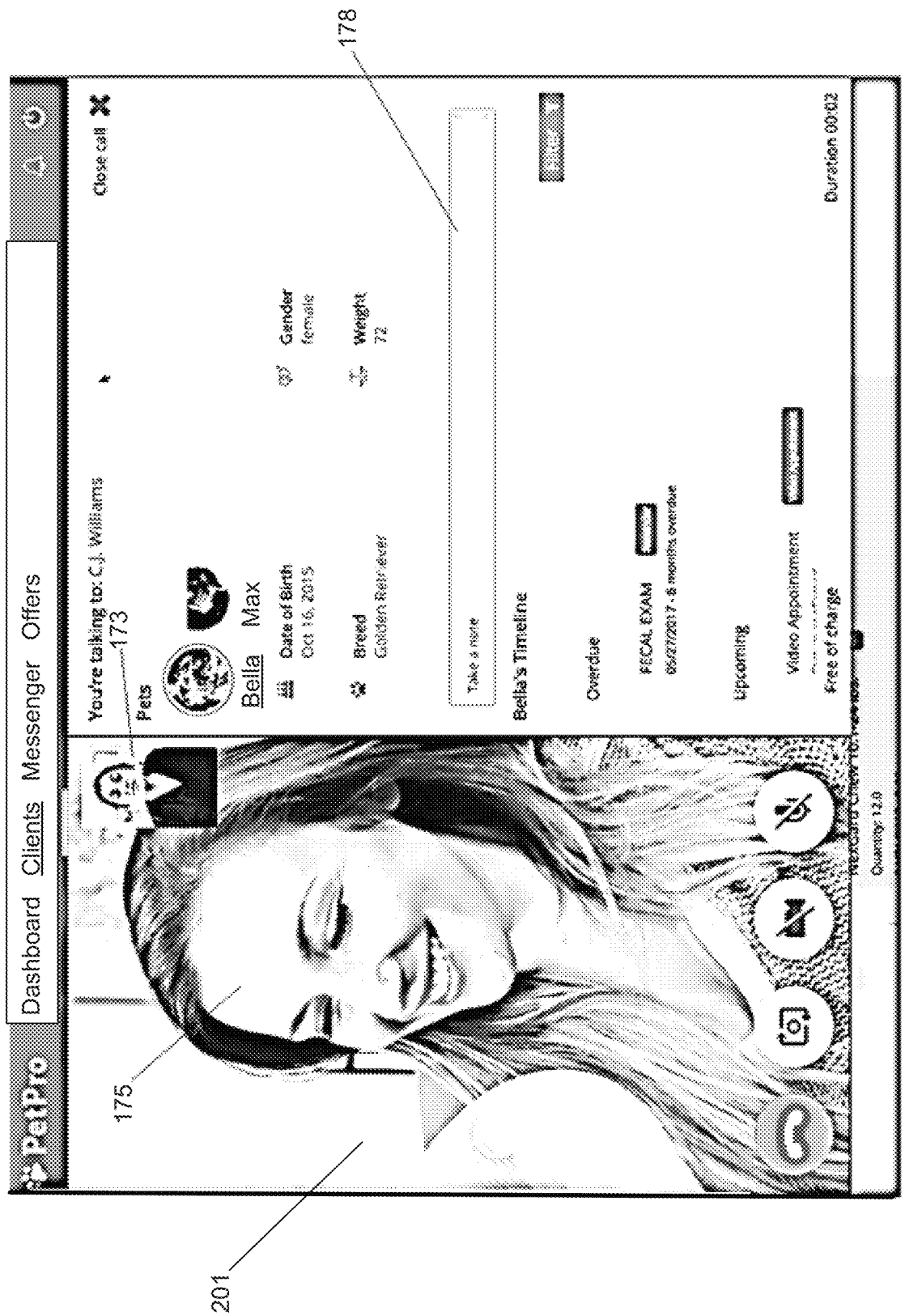
FIG. 1S illustrates a user interface (UI), similar to the UI of FIG. 1R, that may be displayed on the vet desktop device that allows a vet to continue a video call with a pet mobile device being operated by a pet owner.
Figure 1T:
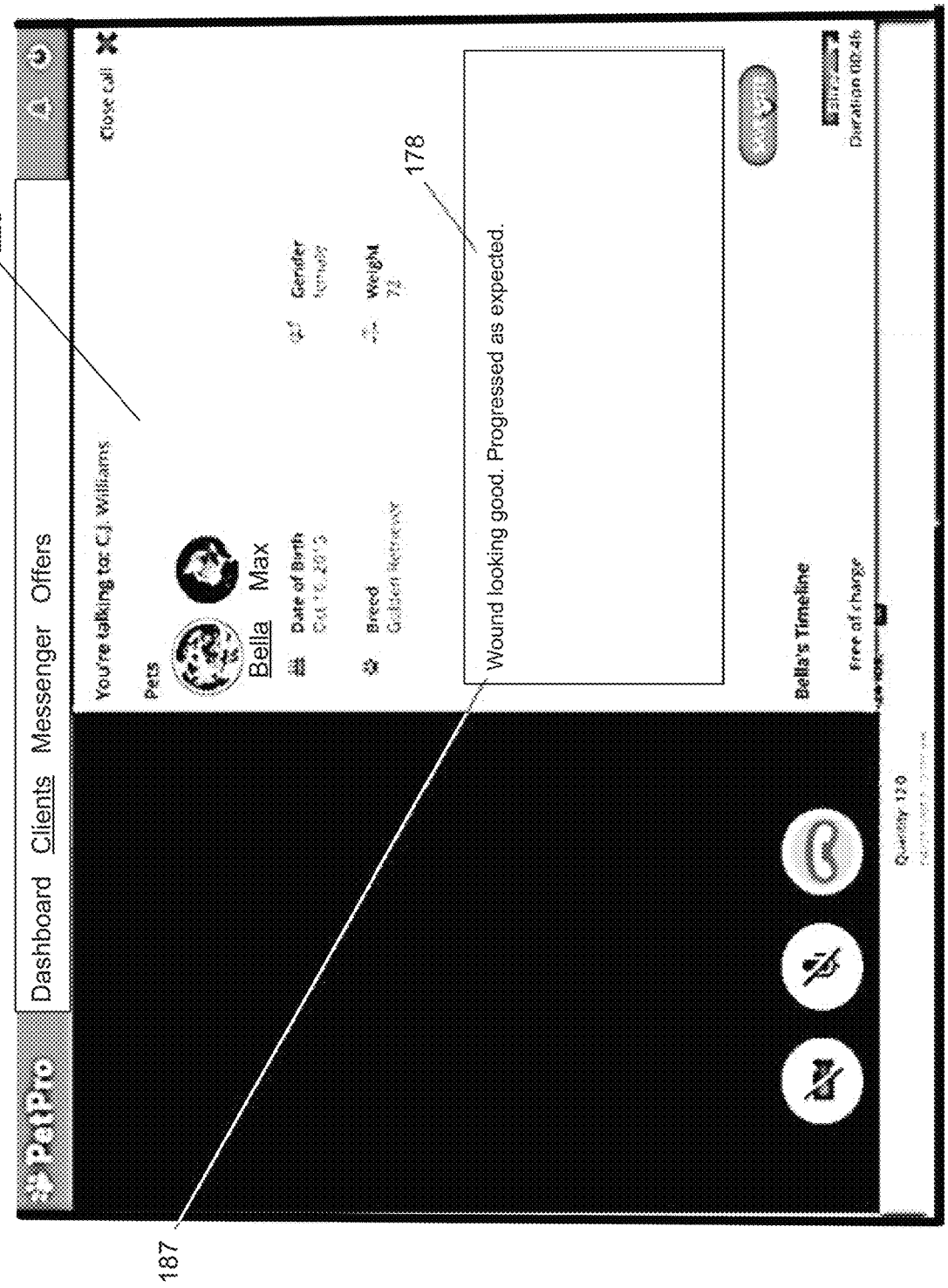
FIG. 1T illustrates a user interface (UI), similar to the UI of FIG. 1R, that may be displayed on the vet desktop device and that allows a vet to end/terminate a video call with a pet mobile device being operated by a pet owner.
Figure 1U:
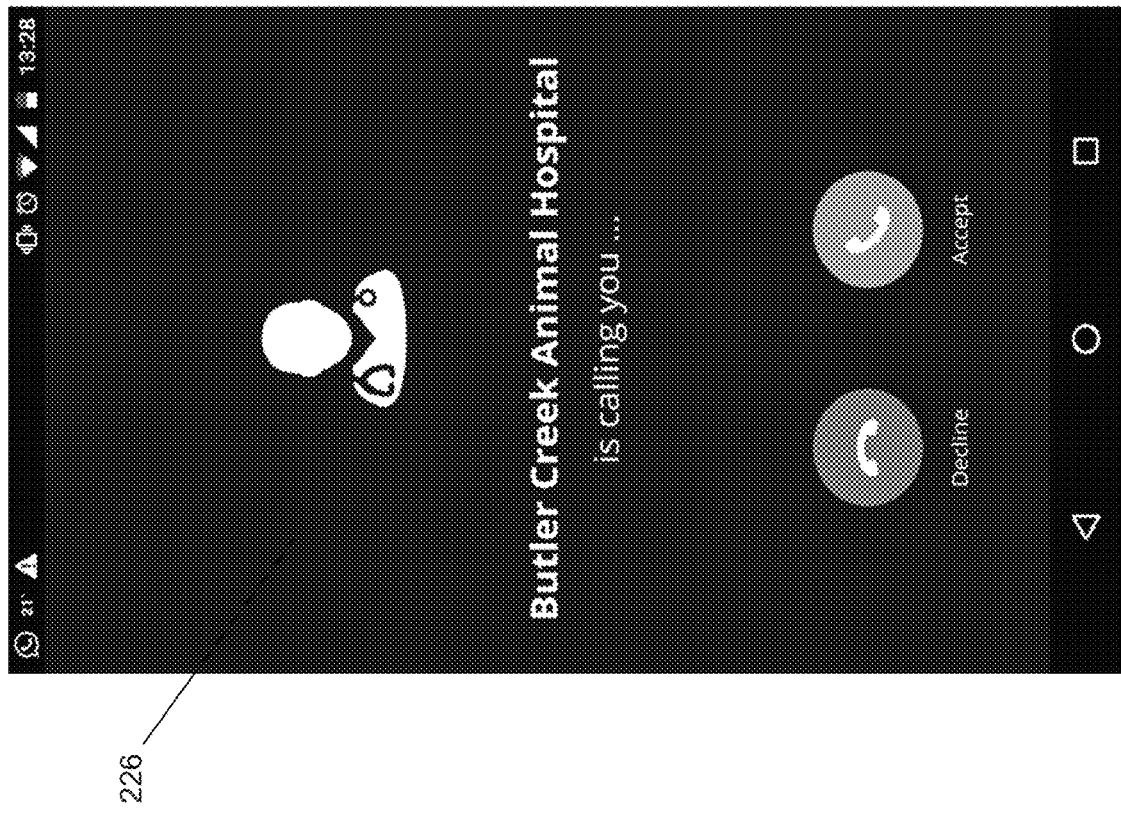
FIG. 1U illustrates a user interface (UI) for the pet owner mobile device such that the mobile device may receive a video call from the vet desktop device.
Figure 2A:
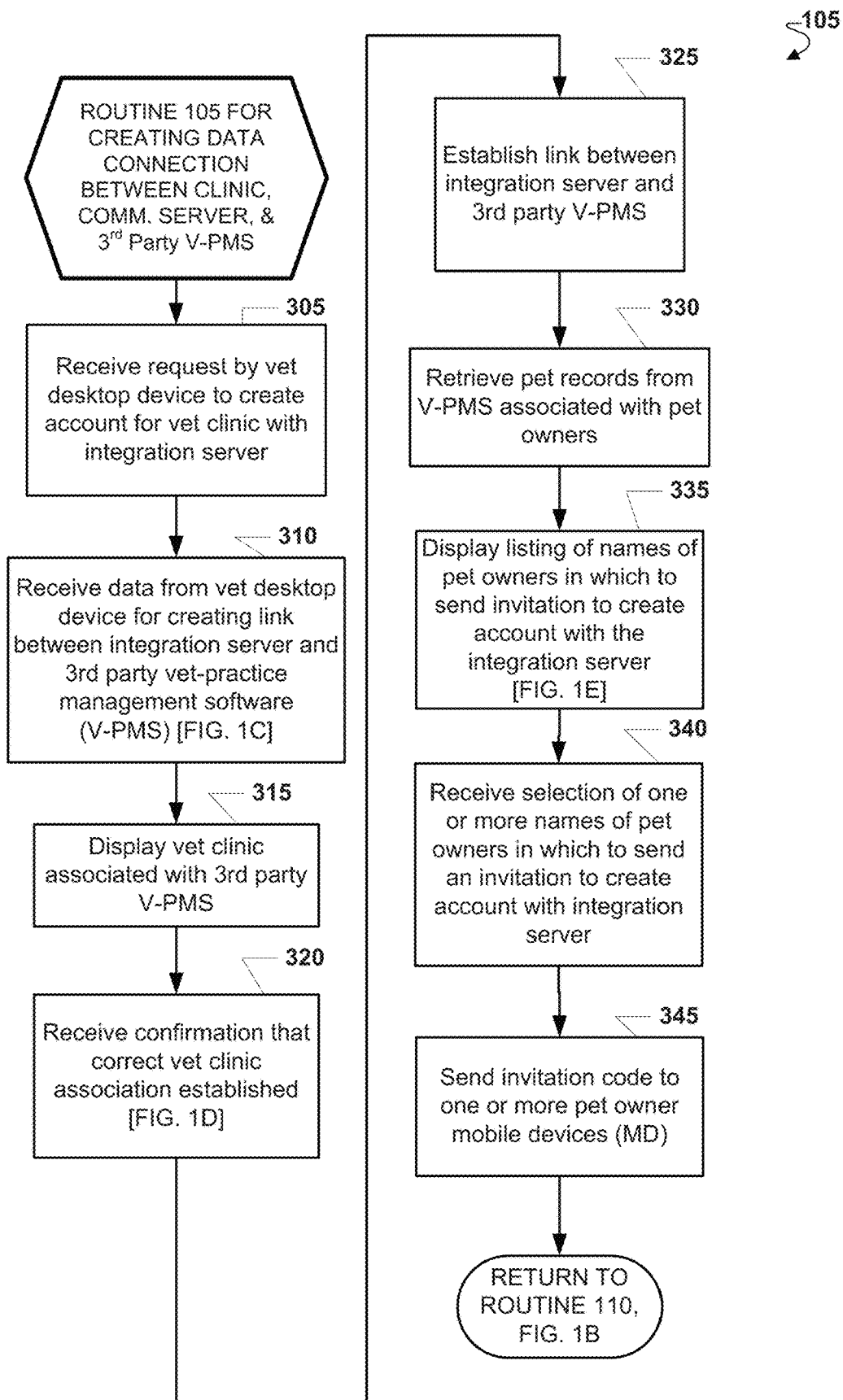
FIG. 2A illustrates steps for a first routine of method illustrated in FIG. 1B in which a data connection is created between the vet desktop device, the integration server, and the third party vet-practice management software (V-PMS)
Figure 2B:
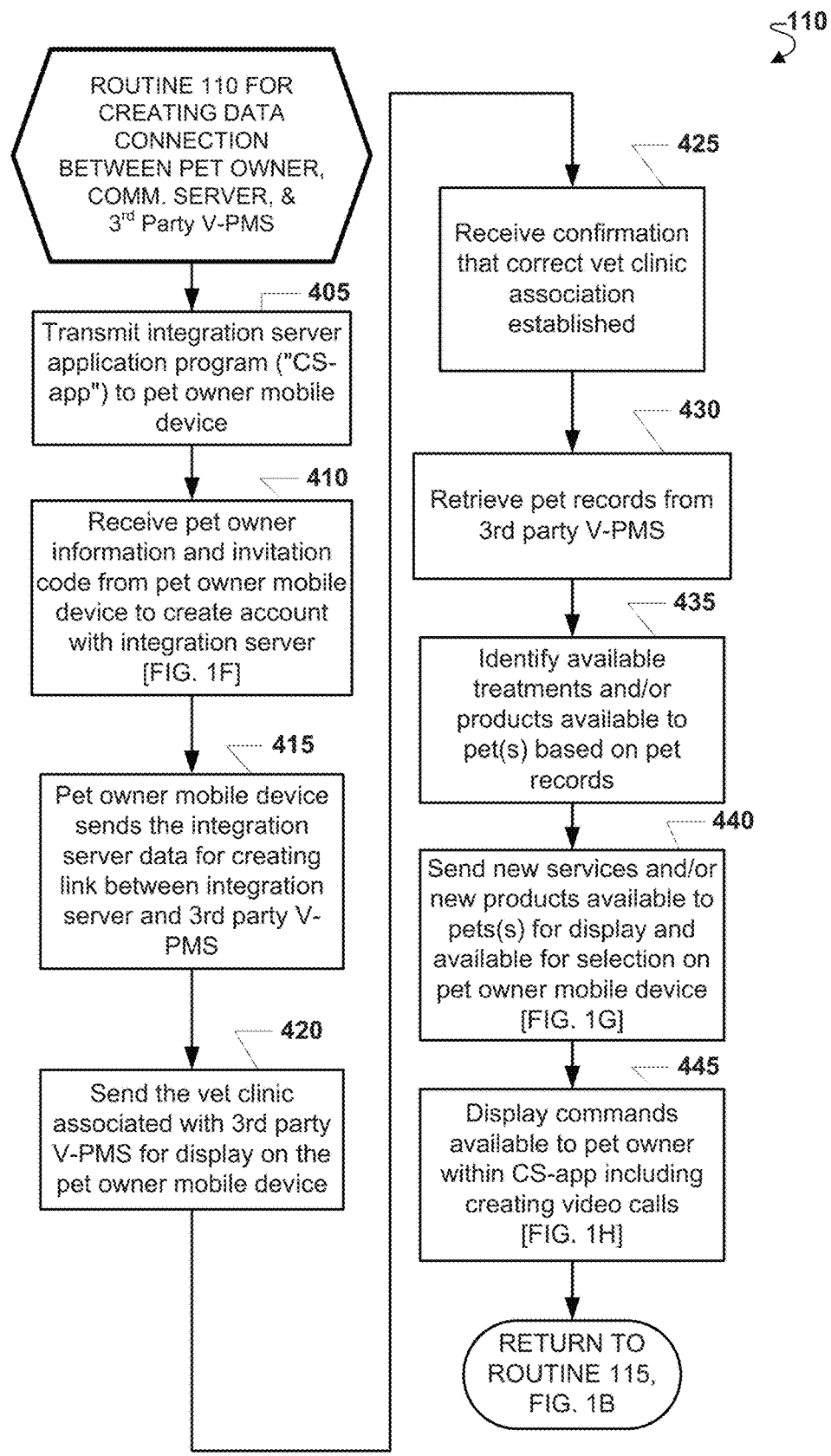
FIG. 2B illustrates the details for the second routine of FIG. 1B in which a data connection is created between the pet owner mobile device, the integration server 201, and the third party vet-practice management software (V-PMS)
Figure 2C:
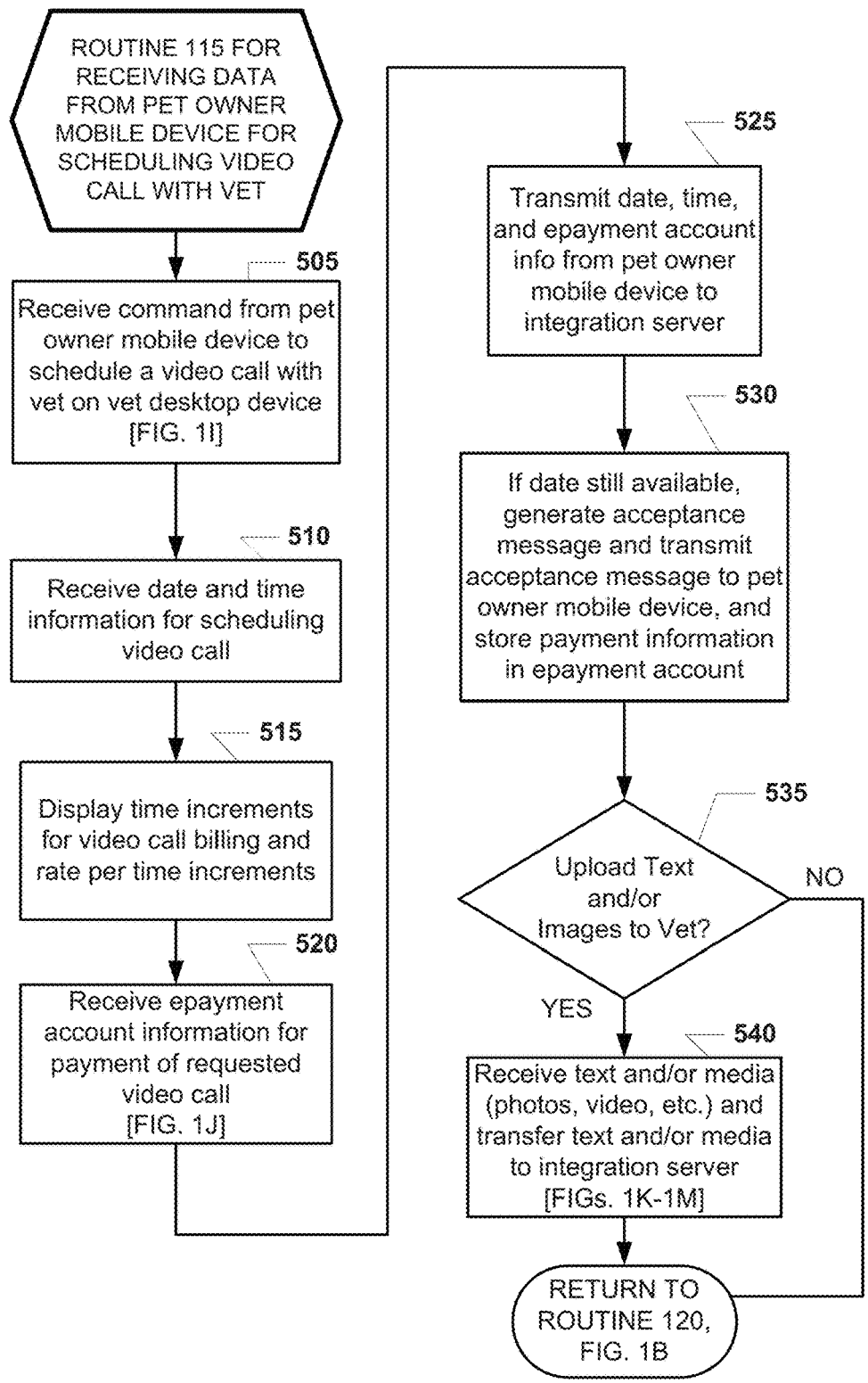
FIG. 2C illustrates the details for the third routine of FIG. 1B in which the pet owner mobile device may receive a command within the integration server application program for scheduling a video call with the vet of the vet clinic.
Figure 2D:
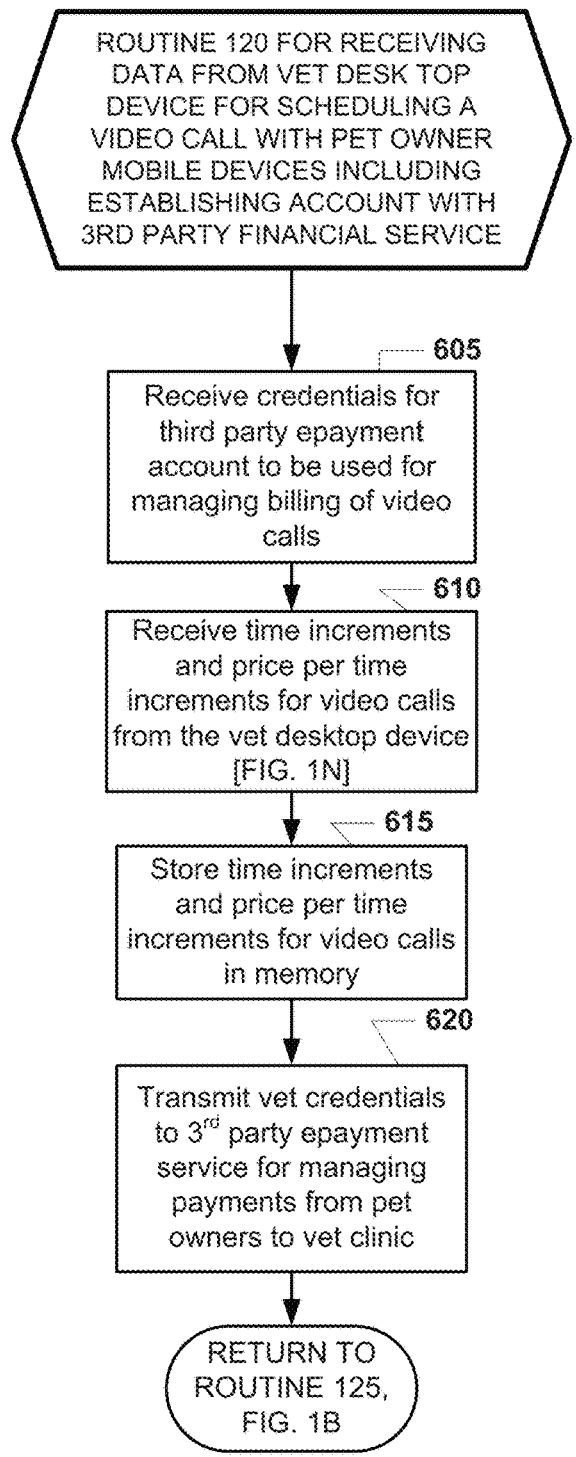
FIG. 2D illustrates the details for the fourth routine of FIG. 1B in which the integration server may receive credentials for the same third party ePayment account service that is used for the pet owner mobile device to manage billing for video calls.
Figure 2E:
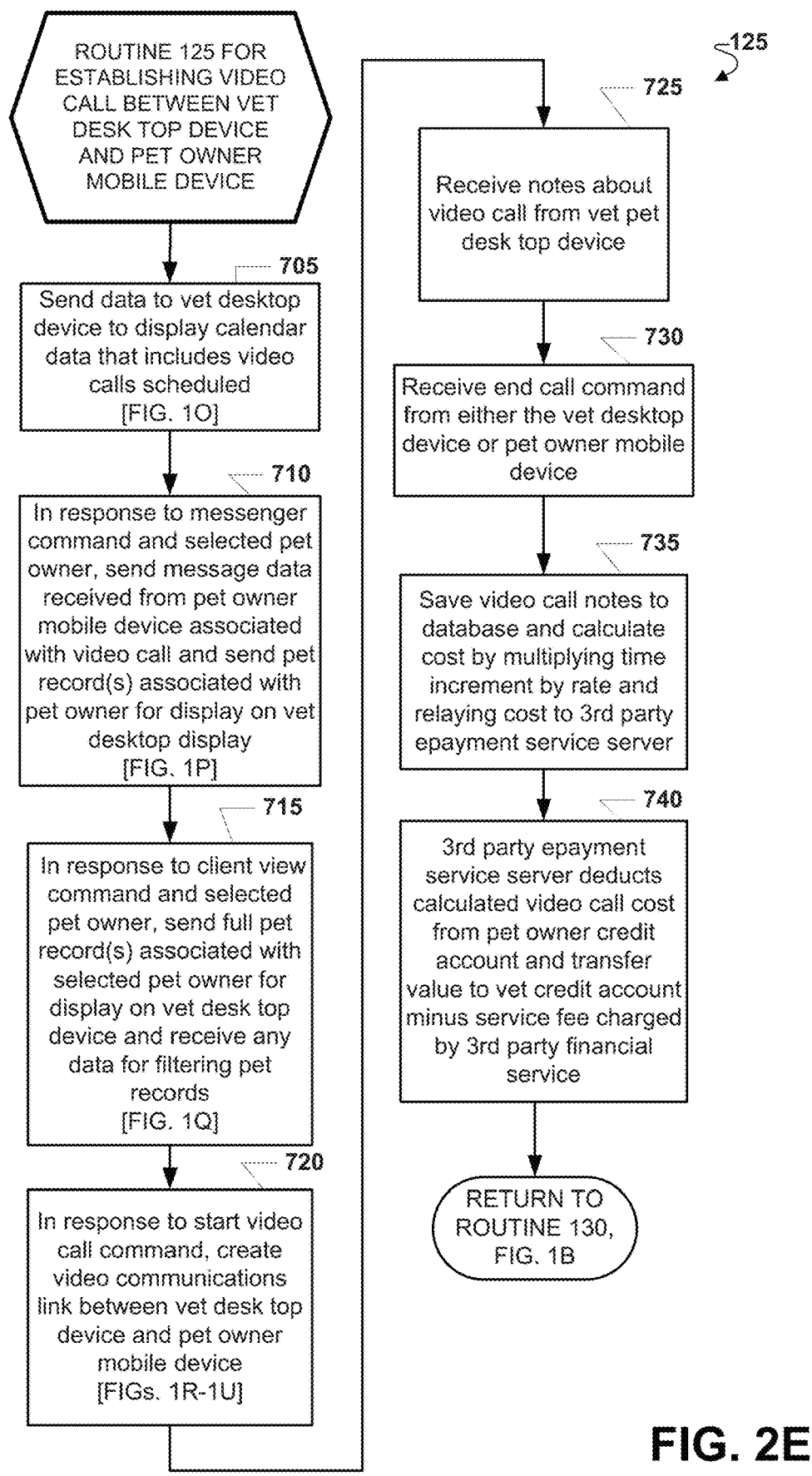
FIG. 2E illustrates further details of the fifth routine of FIG. 1B in which a video call may be established between the vet desktop device and pet owner mobile device.

Further details of routine 125 are illustrated in FIG. 2E described in further detail below. Routine 125 further corresponds with the user interfaces (UIs) of FIGS. 1O-1U which will be described in further detail below.

During routine 125, pet records may be accessed, displayed, reviewed, edited and appended by the vet desktop device 210. The integration server 201C may further receive and save notes produced by the vet desktop device 210. These notes may be prepared before, during, and/or after a video call by the vet desktop device 210.

After routine 125, in routine 130, the integration server 201C may receive a selection of one or more pet products from a pet owner mobile device 205 that may have been suggested by the integration server 201C in routine 110. During routine 130, the integration server 201C may also manage rebates for any selected pet products from the pet owner mobile device 205.

The details for routine 130 are further illustrated in FIG. 2F as will be described below. Routine 130 also generally corresponds to the user interfaces (UIs) of FIGS. 1V-1Z as will be describe in further detail below.

During routine 130, the integration server 201C may manage rebates for products and/or services that the pet owner mobile device 205 ordered from the vet clinic associated with the vet desktop device 210. That is, when a pet owner mobile device 205 orders a product and/or service supplied by vet clinic associate with the vet desktop device 210, the vet clinic using the vet desktop device 210 may verify that a product was delivered and/or service rendered for the pet owner/companion animal.

Once delivery and/or service rendering has been reported to the integration server 201C, the integration server 201C during routine 130 may send a message to the pet owner mobile device 205 that a rebate is available. The pet owner mobile device 205 may then communicate which rebates are desired to be validated. When a rebate is validated, monetary value for the rebate is transferred to a payment account selected by the pet owner mobile device 205 as will be described in more detail below.

At the end of routine 130, the method 100 may return to the first routine 105 and/or any other routines previously described. As noted previously, some of the routines of method 100 may be performed in parallel or in a different sequence. For example, routine 130 which involves managing rebates may occur immediately after routine 110 in which products and/or services that are available for rebate redemption. Further, some routines may be performed in parallel with one another. For example, routine 115 that receives data from the pet owner mobile device 205 for setting up a video call with the vet desktop device 210 may run in parallel with routine 120 where the vet desktop device 210 sets up time increments and price per increments for future video calls. These are just a few examples of how different routines may be executed in a different sequence and/or run in parallel with one another. Other combinations are possible and are included within the scope of this disclosure.

Referring now to FIG. 1C, this figure illustrates an exemplary user interface (UI) 132 that may be displayed on the vet desktop device 210 to receive related account information, including, but not limited to, an e-mail address associated with the vet desktop device 210. This UI 132 may be displayed so that a vet clinic may set up an account with the integration server 201C. The e-mail address entered here should be associated with an account used by a vet with the vet practice management system (V-PMS) 347 (See FIG. 3).

Referring now to FIG. 1D, this figure illustrates an exemplary user interface (UI) 134 that may be displayed on the vet desktop device 210 to confirm V-PMS account information. This UI 132 may be displayed so that a vet clinic may confirm that the integration server 201C has received the correct credentials/login associated with a V-PMS 347 that is used by the vet clinic as will be describe below. This UI 134 may display the name and physical mailing address of the vet clinic the integration server 201C received from the V-PMS 347 (see FIG. 3).

Referring now to FIG. 1E, this figure illustrates an exemplary user interface (UI) 136 that may be displayed on the vet desktop device 210 where the integration server 201C has retrieved a listing of names of pet owners from the V-PMS 347 in which to send an invitation code to create account with the integration server 201C. Access to the integration server 201C by pet owners using pet owner mobile devices 205 is usually by invitation only. That is, according to one exemplary embodiment, a pet owner mobile device 205 may only be able to open a new account with the integration server 201C if the vet desktop device 210 had selected a pet owner mobile device 205 for receiving an invitation comprising an alphanumeric code directly from the integration server 201C or from some other computer.

Figure 1F:
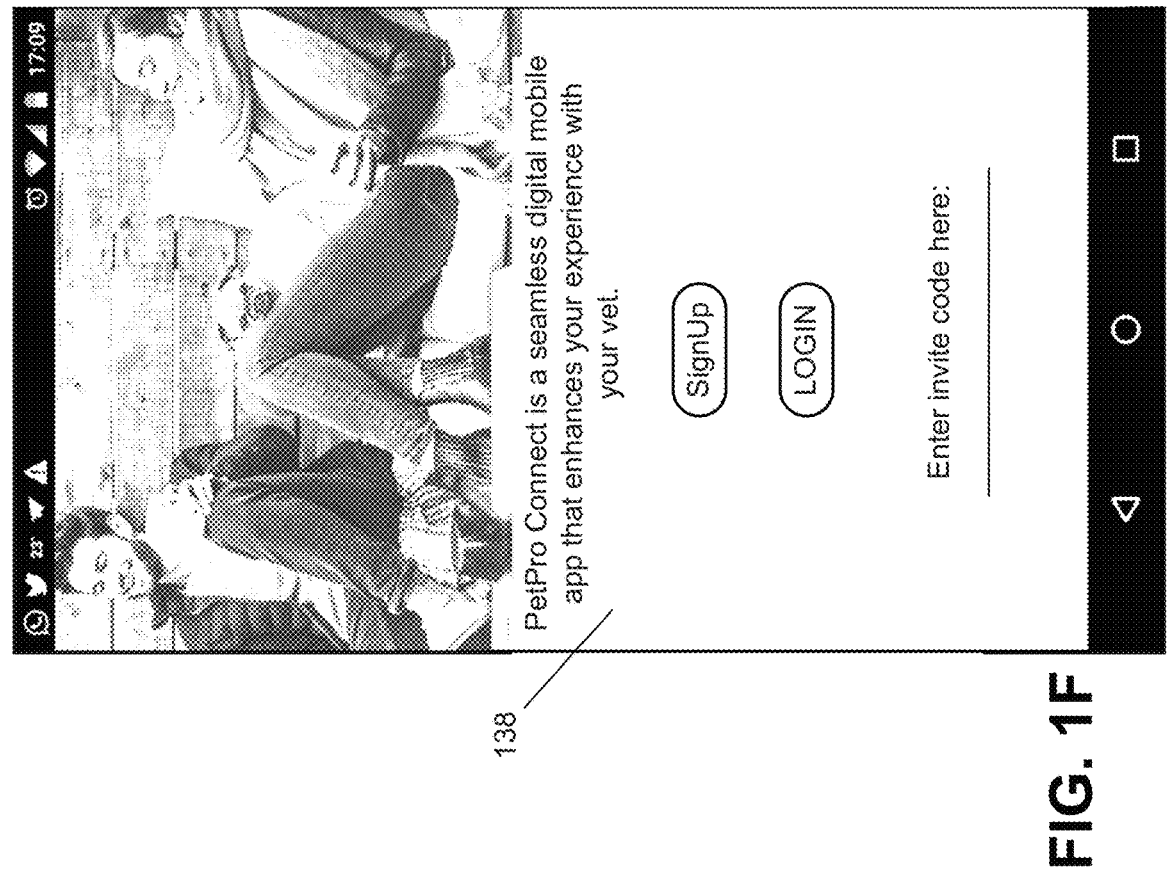
FIG. 1F illustrates an exemplary user interface (UI) that may be displayed on the vet desktop device where the integration server has retrieved a listing of names of pet owners from the V-PMS in which to send invitation to create account with the integration server.

Referring now to FIG. 1F, this figure illustrates an exemplary user interface (UI) 138 that may be displayed on the pet owner mobile device 205 for setting up an account with the integration server 201C by using the invitation code described above in FIG. 1E. UI 138 allows the pet owner mobile device 205 to enter in the alphanumeric invitation code that it received from the integration server 201C via the vet desktop device 210. The pet owner may also create standard log-in credentials as understood by one of ordinary skill in the art (i.e. username & password, etc.).

Referring now to FIG. 1G, this figure illustrates a user interface (UI) 140 that may be displayed on the pet owner mobile device 205 for displaying pet records and suggested products and/or services available from the vet clinic. This exemplary screen display of FIG. 1G illustrates pet records 144 of a companion animal that may be accessed with the PCD/pet owner mobile device 205 by a pet owner. A pet owner can read these pet records 144, however, she cannot annotate or edit these pet records. Once a pet owner creates an account with the system 101, then the pet owner is provided with read-only access to the entire pet medical history that was created by a particular vet clinic which has treated the companion animal.

FIG. 1G further illustrates rebate icons 142 associated with pet products/services that may be displayed with the medical history of the companion animal. These rebate icons 142 of FIG. 1G may be selected by the pet owner in order to redeem rebates associated with a selected pet products and/or pet services available from the vet clinic as will be described in detail below.

Exemplary pet products may include, but are not limited to, pet supplements that may include vitamins, pet medicines, pet collars, and other pet devices that may be sold by a vet clinic. Exemplary services include, but are not limited to, parasitic treatments (i.e. flea baths), boarding for the companion animal, vaccinations, and pet supplements.

Exemplary records/data that are managed by the system 101 and that may be displayed with UI 140 may include parameters such as, but not limited to, height, length, width, girth, weight, color, fertility status (i.e.—pregnant, not pregnant . . . etc.) and other physical characteristics of the animal, as well as treatments, such as vaccine data, drug treatment data, cleanings, health issues, surgeries, feeding information etc.

Figure 1H:
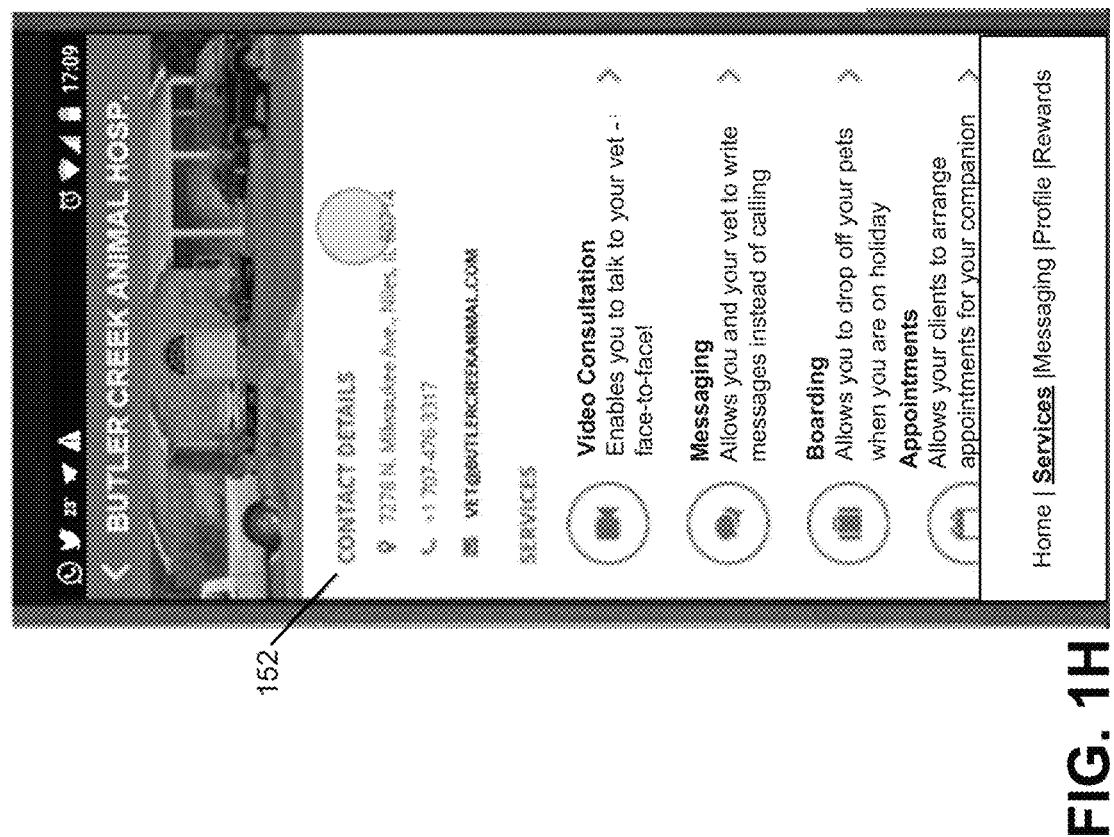
FIG. 1H illustrates a user interface (UI) that may be displayed on the pet owner mobile device for listing available commands for the downloadable client software which provides access to the integration server.
Figure 1I:
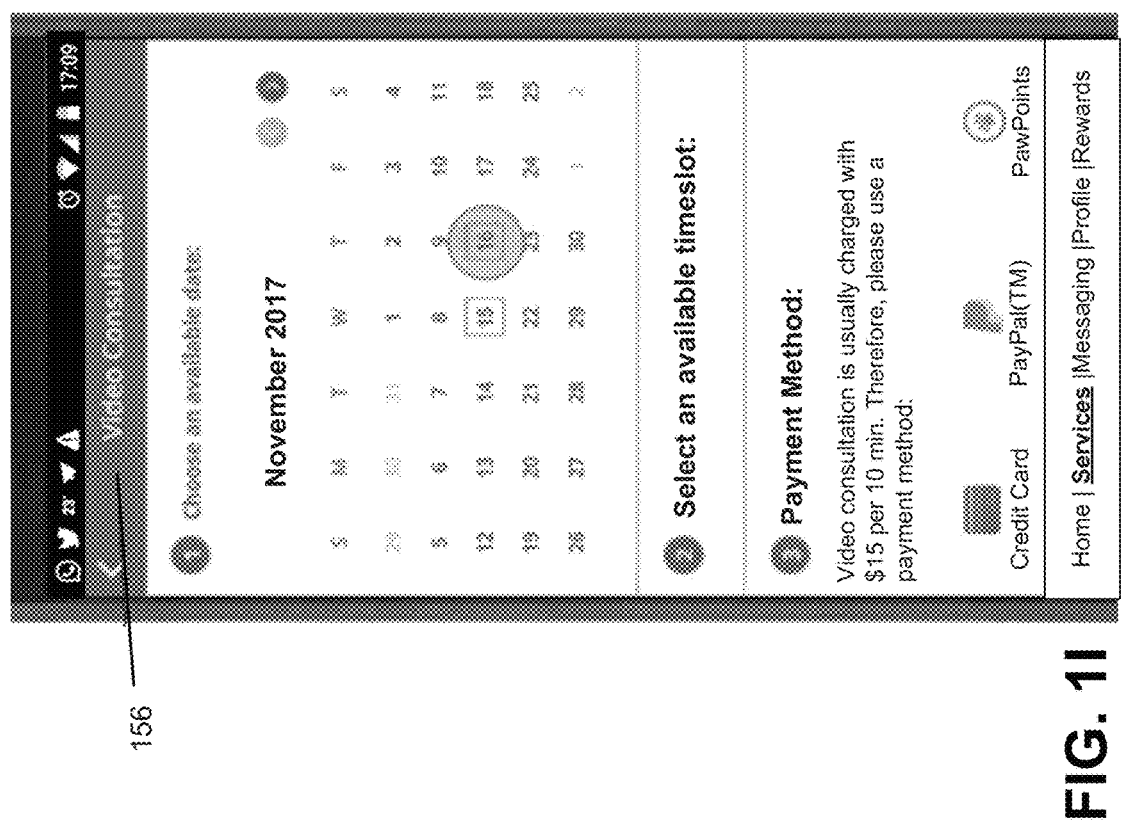
FIG. 1I illustrates a user interface (UI) that may be displayed on the pet owner mobile device for setting up a video consult with a vet via the vet desktop device.
Figure 1K:
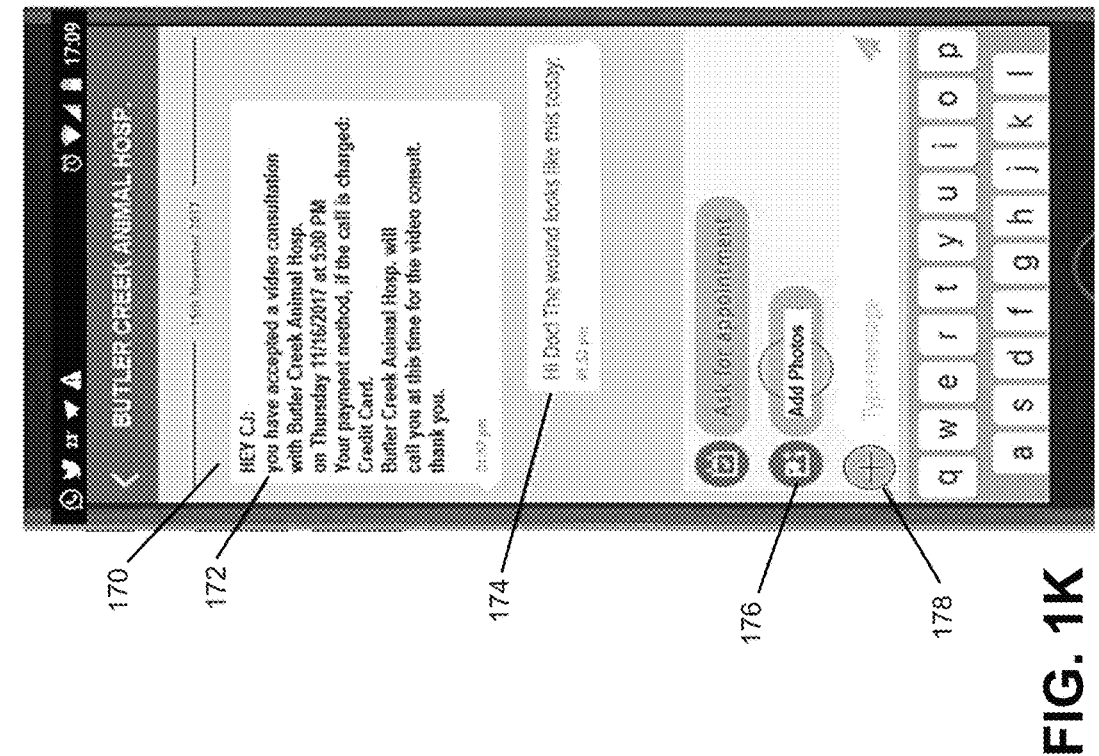
FIG. 1K illustrates a user interface (UI) that may be displayed on the pet owner mobile device for sending a text message and/or media to a vet via the vet desktop device.
Figure 1J:
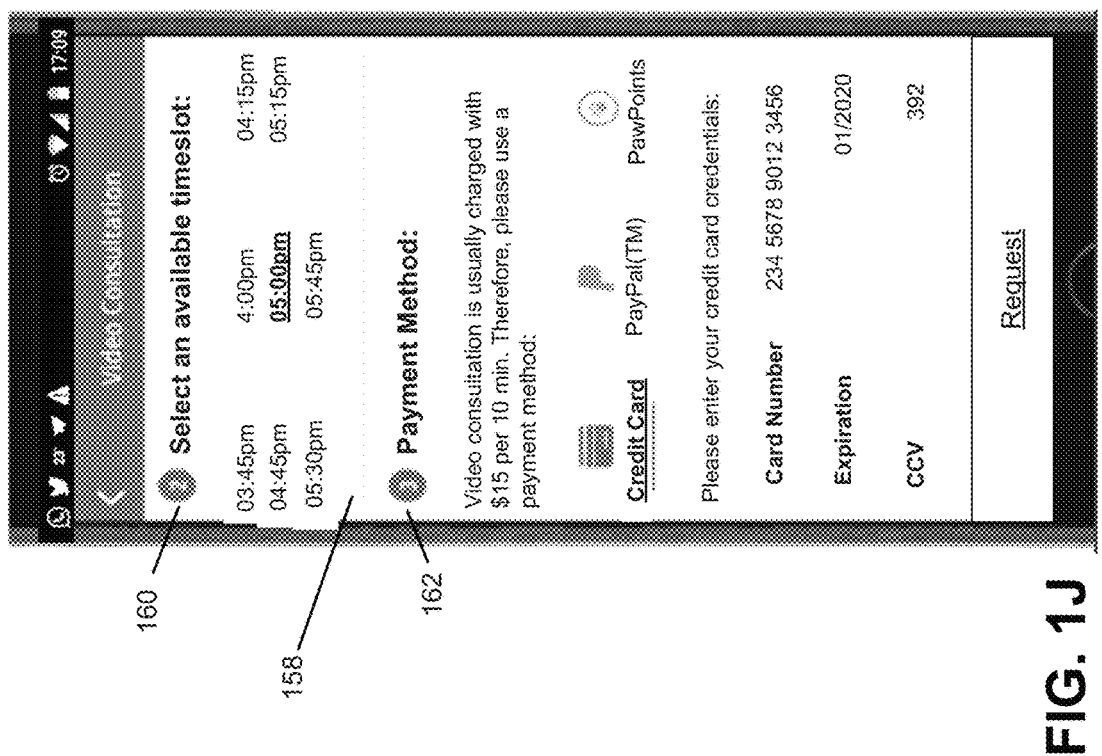
FIG. 1J illustrates a user interface (UI) that may be displayed on the pet owner mobile device for setting up a video consult with a vet via the vet desktop device, similar to the UI of FIG. 1I.
Figure 1M:
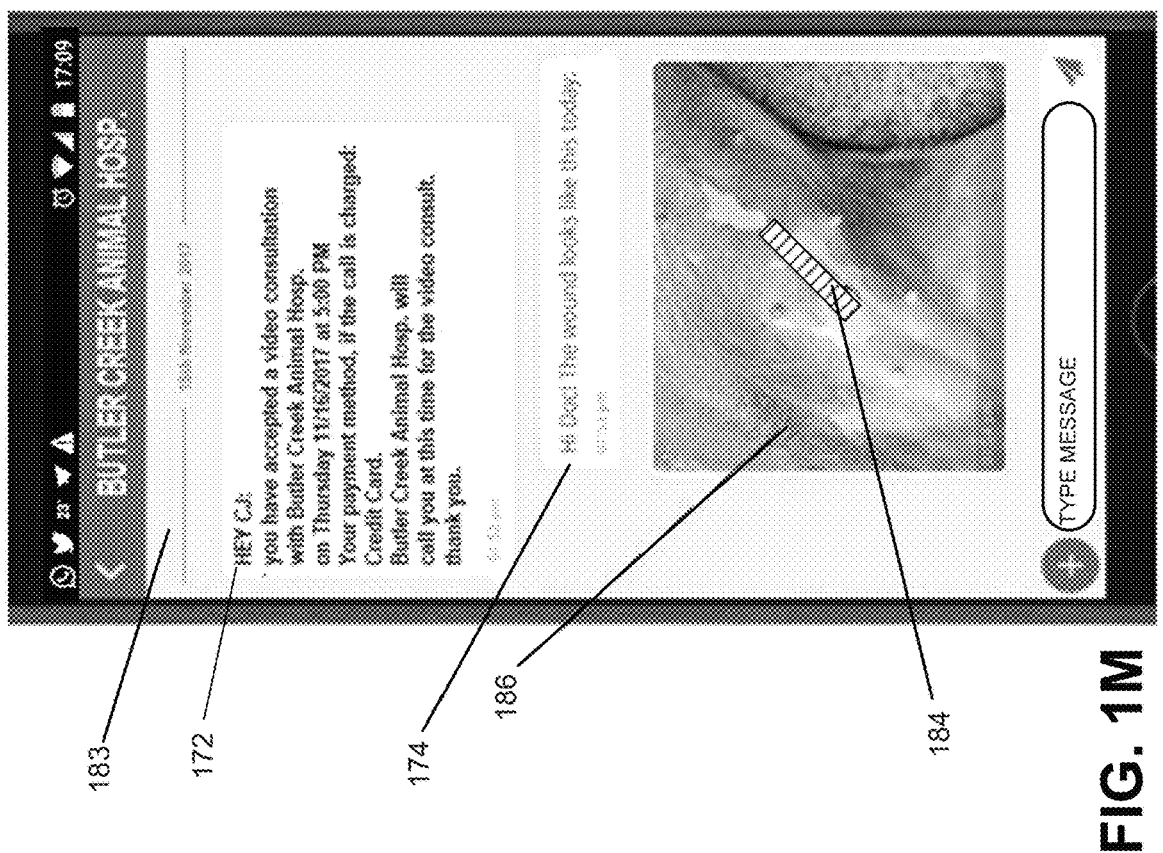
FIG. 1M illustrates a user interface (UI) that may be displayed on the pet owner mobile device showing media (i.e. photographs and/or video) that has been selected for upload to the integration server for eventual display on the vet desktop device.
Figure 1L:
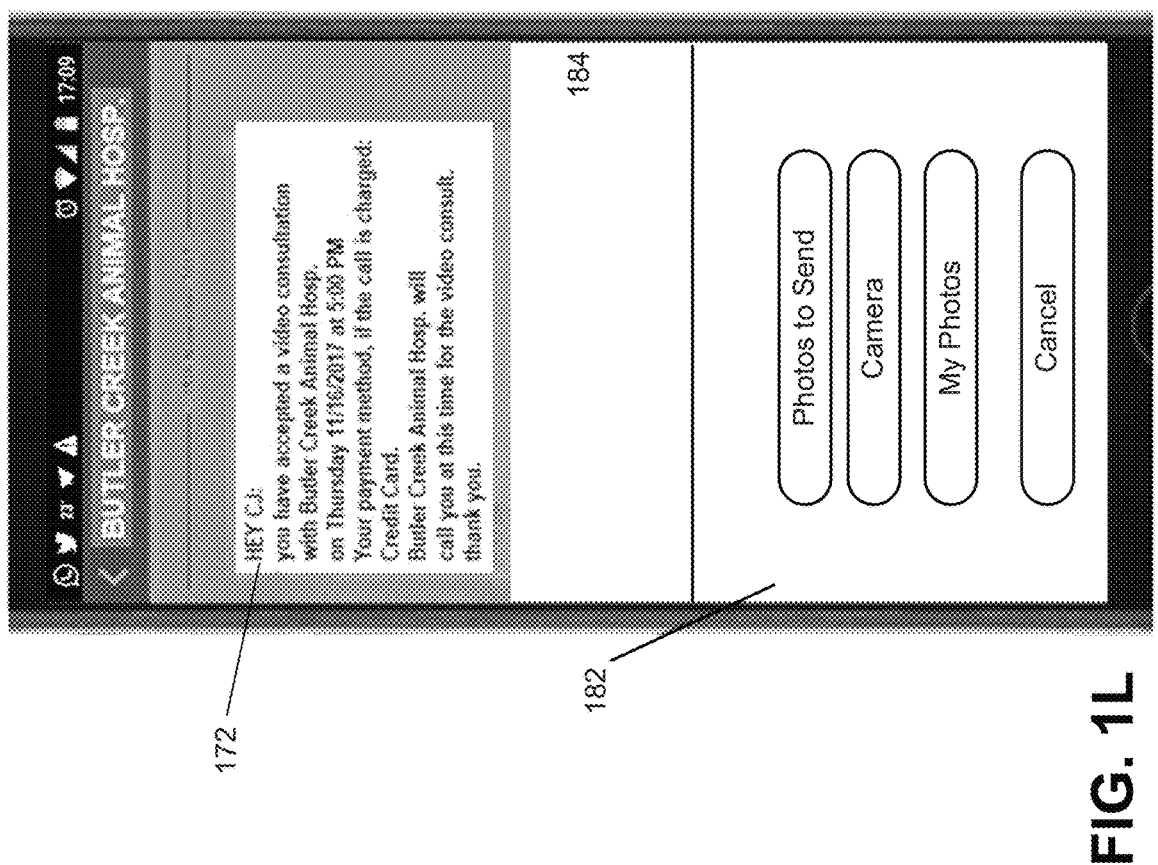
FIG. 1L illustrates a user interface (UI) that may be displayed on the pet owner mobile device for uploading media (i.e. photographs and/or video) to the integration server for eventual display on the vet desktop device.
Figure 1N:
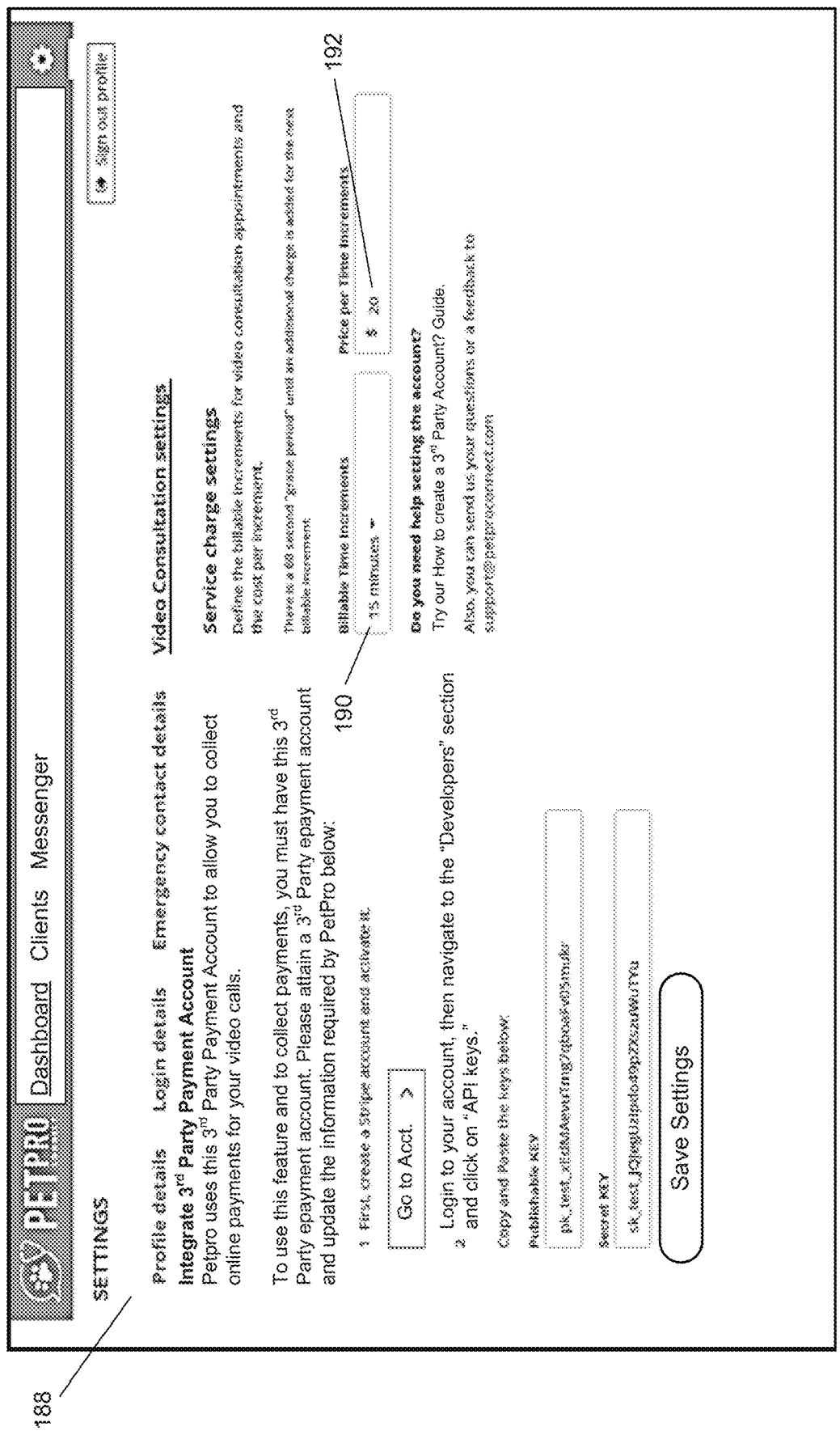
FIG. 1N illustrates a user interface (UI) that may be displayed on the vet desktop device for establishing a communication link with a third party Epayment provider for managing billing of video calls for the vet desktop device.
Figure 10:
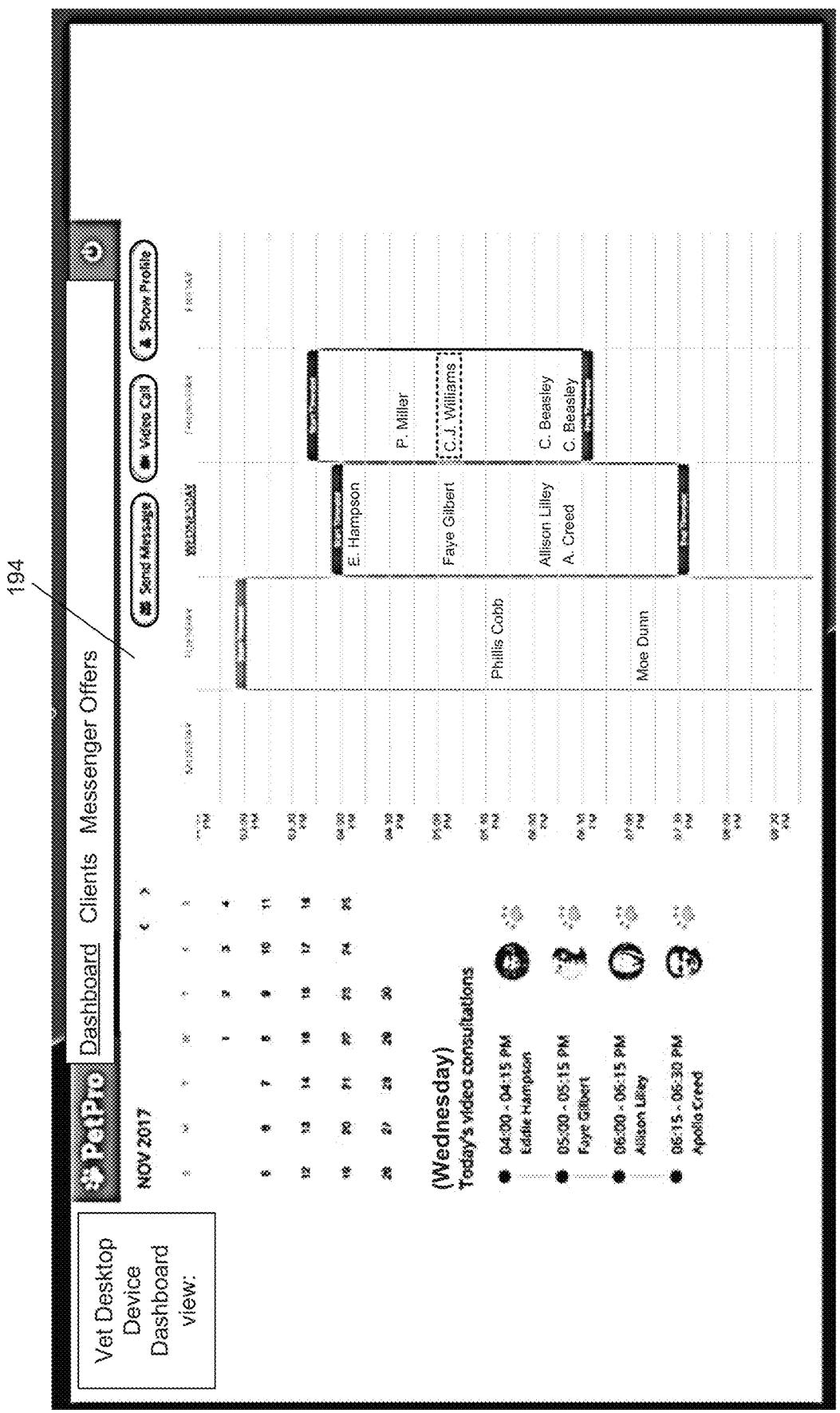
Figure 1V:
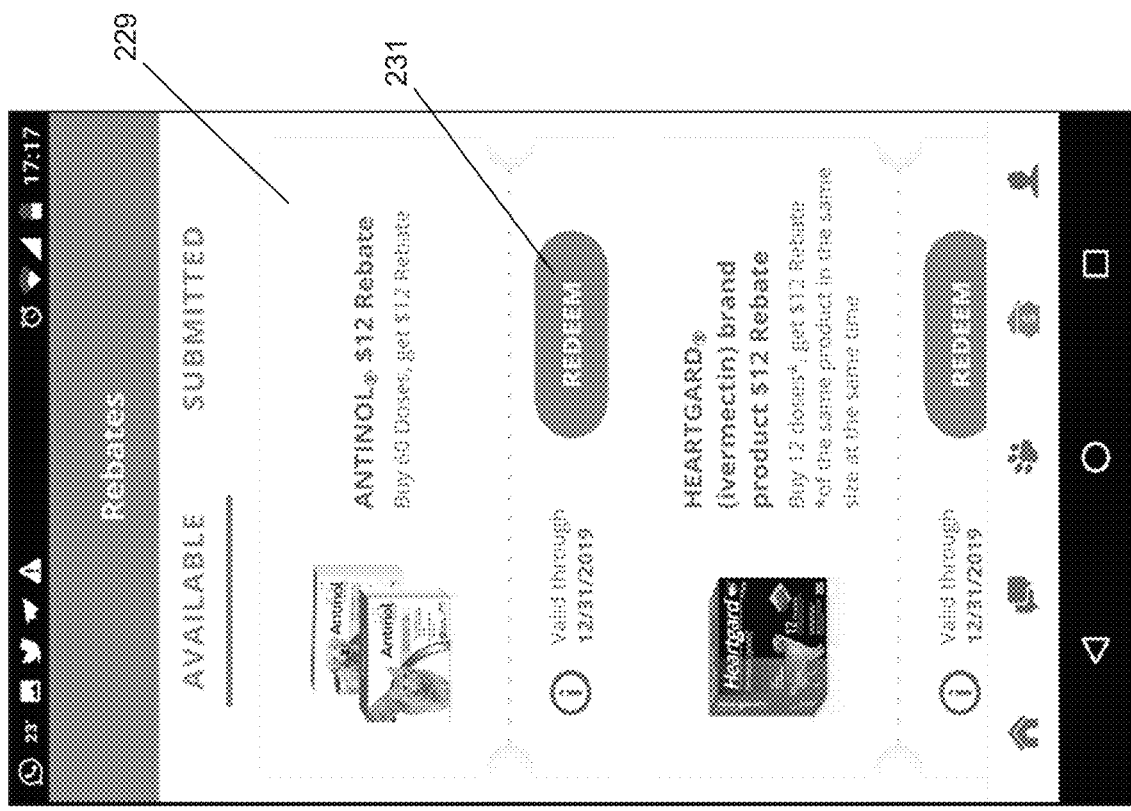
FIG. 1V illustrates a user interface (UI) that may be displayed on the pet owner mobile device that allows a pet owner to redeem rebates for products and/or services that were bought from the vet clinic.
Figure 1X:
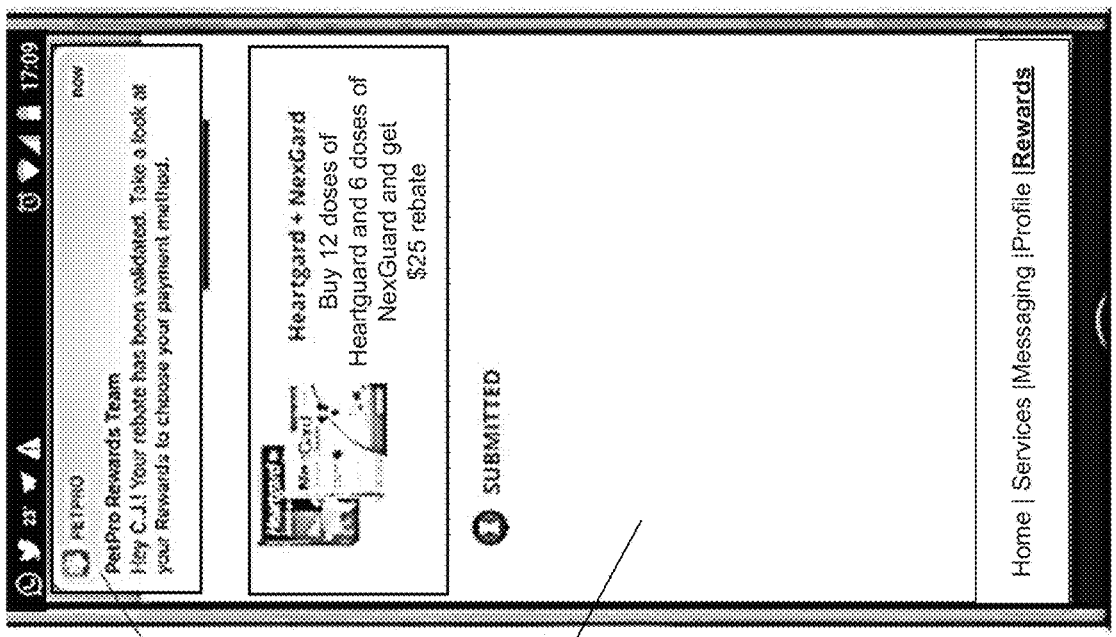
FIG. 1X illustrates a user interface (UI) that may be displayed on the pet owner mobile device which displays an incoming message from the integration server that the rebate submitted in the UI of FIG. 1W has been validated/approved by the vet desktop device.
Figure 1W:
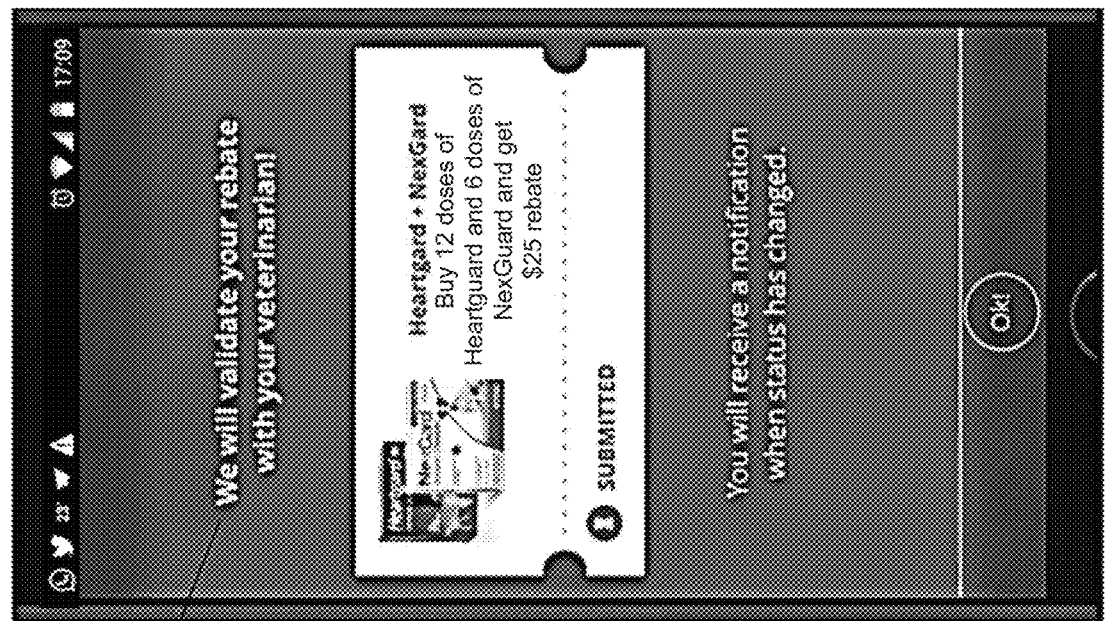
FIG. 1W illustrates a user interface (UI) that may be displayed on the pet owner mobile device which lists a message that the rebate selected in FIG. 1V has been sent to the vet desktop device for validation/redemption.

Referring now to FIG. 1H, this figure illustrates a user interface (UI) 152 that may be displayed on the pet owner mobile device 205 for listing available commands for the downloadable client software 201B, which provides access to the integration server 201C. The commands for the software 201B include, but are not limited to, video calls, messaging the vet desktop device 210, boarding services from the vet clinic for the companion animal, and setting up future vet appointments at the vet clinic. Further details for these exemplary commands of FIG. 1H will be described below.

Figures 1, 1Y, 2:
Figures 1, 1Y:
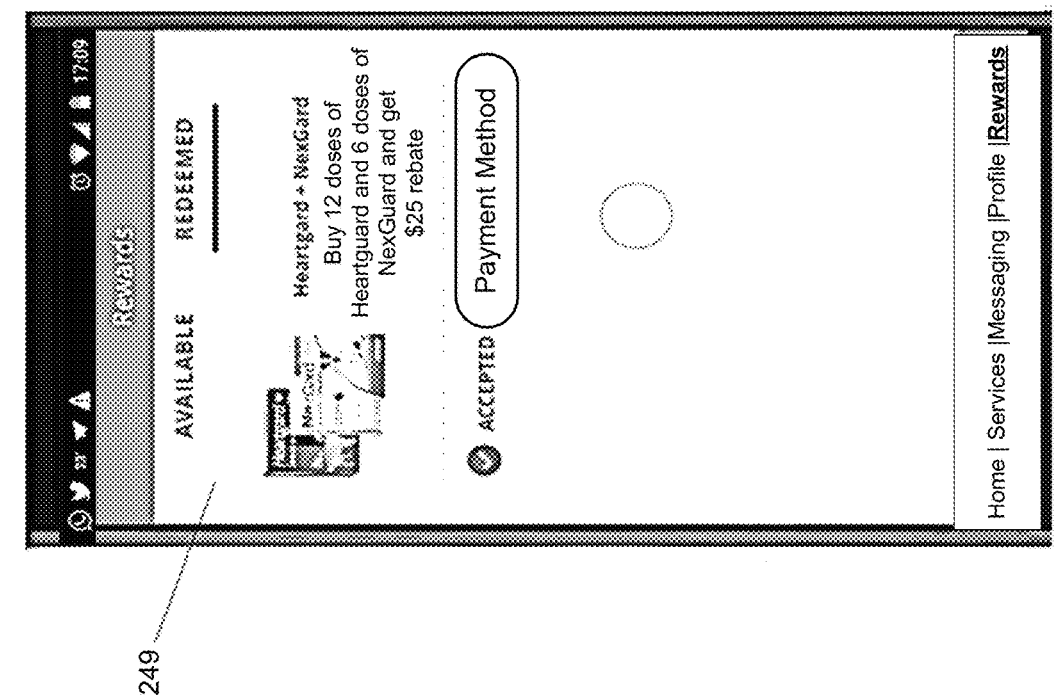
FIG. 1Y-1 illustrates a user interface (UI) that may be displayed on the pet owner mobile device which displays a rewards function that includes rebates which have been accepted or validated by the vet desktop device.
Figure 1Z:
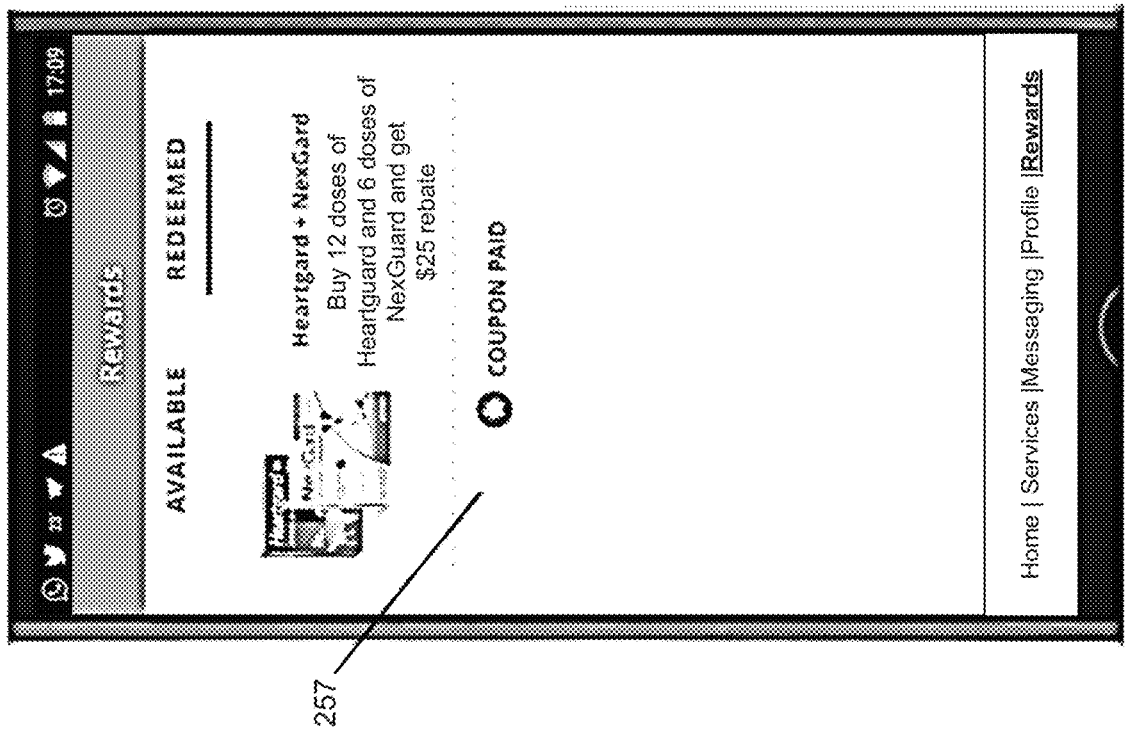
FIG. 1Z illustrates a user interface (UI) that may be displayed on the pet owner mobile device which provides a message that the value of the rebate has been paid/redeemed to the financial account selected in the UI of FIG. 1Y-2.

Referring now to FIG. 1, this figure illustrates a user interface (UI) 156 that may be displayed on the pet owner mobile device 205 for setting up a video consult with a vet via the vet desktop device 210. The UI 156 may allow a pet owner to set up a video consultation with the vet of the vet clinic. The pet owner may select a date on a calendar and the system may display available times for the vet for a particular date selected. The pet owner may select a time and then "lock" or confirm the video consultation by providing a payment method for the video consultation. The payment method may include a financial card (i.e. bank, credit, or debit card) which may have been previously loaded by the pet owner into the system 101. Further details about setting up a video call will be described below.

Referring now to FIG. 1J, this figure illustrates a user interface (UI) 158 that may be displayed on the pet owner mobile device 205 for setting up a video consult with a vet via the vet desktop device 210, similar to the UI of FIG. 1I. This UI 158 may be generated in response to the "select an available timeslot" command of UI 156 of FIG. 1I. The UI 160 now lists available times 160 for the vet in which to conduct a video call. The UI 158 further includes the payment method command that is also present in UI 156 of FIG. 1I. In this UI 158, the user has entered a card number for a financial account, which can include, but is not limited to, a bank account, a credit card, a debit card, a PAYPAL™ online account, etc.

Referring now to FIG. 1K, this figure illustrates a user interface (UI) 170 that may be displayed on the pet owner mobile device 205 for sending a text message and/or media to a vet via the vet desktop device 210. This UI 170 may be generated in response to a pet owner mobile device 205 issuing a "messaging command" to the integration server 170 such that a pet owner may send a text message and/or media (i.e. photographs and/or video) that the pet owner would like the vet to review prior to a video consult. See "messaging command" in bottom portion of FIG. 1I, showing the available commands, as just one example of where this command may be selected on the pet owner mobile device 205.

The UI 170 may display a confirmation message 172 that the integration server 201C may have issued in response to a vet desktop device accepting the prior video call request. The text message UI 170 allows the pet owner mobile device 205 to author a text message 174. Here, in this exemplary text message 174, the pet owner is alerting the vet that she would like the vet to review the healing of a wound on a companion animal in which the vet may have used stitches to close the wound. The UI 170 allows the pet owner mobile device 205 to upload media via the upload media on-screen button 170. The pet owner mobile device 205 may further add additional text with the add text command 178 visible in UI 170.

Referring now to FIG. 1L, this figure illustrates a user interface (UI) 182 that may be displayed on the pet owner mobile device 205 for uploading media (i.e. photographs and/or video) to the integration server 201C for eventual display on the vet desktop device 210. The UI 182 may list a plurality commands for accessing files on the pet owner mobile device 205 for uploading. Exemplary commands include, but are not limited to, photos to send, files from the camera of the mobile device 205, my photos [specific file directories on the mobile device 205], etc.

Referring now to FIG. 1M, this figure illustrates a user interface (UI) 183 that may be displayed on the pet owner mobile device 205 showing media (i.e. photographs and/or video) that has been selected for upload to the integration server 201C for eventual display on the vet desktop device 210. The message 172 from the integration server 201C and message 174 by the pet owner mobile device 205 were previously described.

The UI 183 is generated in response to a pet owner selecting a file from the list of file options displayed in the UI 182 of FIG. 1M. The UI 183 of this exemplary embodiment shows a digital photograph 186 that the pet owner, C. J. Williams (in this example), has taken of her companion animal. The digital photograph 186 comprises a belly underside of the companion animal which may have a series of stitches 184 from a surgical incision.

This photograph 186 of FIG. 1M is consistent with the pet owners prior text message 174, which states, "Hi Doc! The wound looks like this today:" One of ordinary skill in the art recognizes that other media types may be used, such as video, and that photographs different than shown in this example/exemplary embodiment are possible and are included within the scope of this disclosure.

Referring now to FIG. 1N, this figure illustrates a user interface (UI) 188 that may be displayed on the vet desktop device 210 for establishing a communication link with a third party Epayment provider for managing billing of video calls for the vet desktop device 210. With UI 188, a vet and/or an admin for the vet clinic may set up an account with a third party, off-the-shelf Epayment platform. One exemplary Epayment platform available as of this writing, and used within system 100, has been sold under the brand name of the STRIPE™ payment platform. Further details of the third party, STRIPE™ payment platform may be found at the following URL: https://stripe.com/.

With UI 188 of FIG. 1N, the vet desktop device 210 may set the time increments 190 for billing video calls with the pet owner mobile devices 205. Exemplary time increments include, but are not limited to, fractions of the hour. But other increments are possible such as fractions of blocks of hours, or fractions of minutes, etc. Accordingly to the exemplary embodiment illustrated in FIG. 1N, the time increments 190 presented may be in the form of a drop down menu where the menu may list several different minute increments, such as, but not limited to, increments of an hour in ten minute blocks, or increments of an hour in fifteen minute blocks. Other configurations are possible and are included within the scope of this disclosure as understood by one of ordinary skill in the art.

The UI 188 of FIG. 1N also provides a price per time increments 192. The vet desktop device 110 may input any price for the price per time increments 192. The price per time increments 192 may be adjusted at anytime by the vet desktop device 210.

Referring now to FIG. 1O, this figure illustrates a user interface (UI) 194 that may be displayed on the vet desktop device 210 for displaying calendar data, including information about past, present, and future video calls scheduled with a vet desktop device 210. The UI 194 may show upcoming video consults with pet owner mobile devices 205 as well as the pet medical records associated with the companion animals of the pet owners.

A pet owner, CJ Williams, in UI 194 of FIG. 1O has been highlighted with a dashed rectangular box to show that this pet owner was selected for review by the vet desktop device 210 so that messages may be sent to or received from this pet owner. Portions of the companion pet medical records may also be visible after a pet owner is selected from the this calendar view of UI 195 as will be described below.

Referring now to FIG. 1P, this figure illustrates a user interface (UI) 196 that may be displayed on the vet desktop device 210 for displaying messages 174 received from pet owner mobile devices 205 and for review by a vet prior to a video call. In the exemplary UI 196 of FIG. 1P, the message 174 created by the pet owner and a photo 186 showing a wound 184 of a companion animal are now visible on the vet desktop device 210 for review by the vet. Message 174 and photo 186 were described above where the pet owner mobile device 205 uploaded this data in connection with the request for the video call as illustrated in FIG. 1M described above.

Also displayed in the UI 196 of FIG. 1P is a listing of the pet owner 165 with highlighted or bolded text to show this pet owner 165 and her text messages 174 are now being displayed. Also visible in this UI 196 are the two companion pets named Bella and Max and portions of their pet records.

One of the two companion pets may be highlighted with an underline to show that this animal's records are now visible. In the exemplary embodiment of FIG. 1P, the dog named Bella is highlighted and corresponding information from her pet records are displayed, including, but not limited to, Date of Birth, Gender, Breed, Weight, and a timeline 167 which may list, in chronological order, treatments and/or exams that were given to Bella from the vet clinic. The UI 196 also allows the vet desktop device 210 to insert any notes that the vet may have after reviewing the message 174 from the pet owner mobile device 205.

Referring now to FIG. 1Q, this figure illustrates a user interface (UI) 198 that may be displayed on the vet desktop device 210 for reviewing pet medical records in more detail. This user interface 198 may be produced in response to the "Clients" command selected from the command bar at the top of the webpage. Alternatively, this UI 198 may be generated by double-clicking the pet owner name 165 found in the UI 196 of FIG. 1P.

In the exemplary embodiment of FIG. 1Q, the selected pet owner is C. J. Williams. As noted previously in connection with the UI 196 of FIG. 1P, the pet owner C. J. Williams, according to this exemplary embodiment, has two companion animals/pets being tracked by the integration server 201C. According to this embodiment, the first pet 169 of Bella and the dog's corresponding pet medical records are being displayed on the vet desktop device 210.

A filter 171 for filtering the medical records is now visible in this UI 198 of FIGS. 1Q and 1s available for selection by the vet. Exemplary parameters for the filter 171 may include, but are not limited to, Exams, Practice Appointments, Prescriptions, Reminders, Surgeries, Vaccinations, and Video Appointments, just to name a few. Other parameters are possible and are included within the scope of this disclosure.

Referring now to FIG. 1R, this figure illustrates a user interface (UI) 199 that may be displayed on the vet desktop device 210 that allows a vet 173 to initiate a video call with a pet mobile device 205 being operated by a pet owner 175. With this UI 199, the vet desktop device 210 initiated the video call with the pet owner mobile device 205 by selecting the "start video call" button of the UI 198 of FIG. 1Q (see top of page of FIG. 1Q near right side). With the UI 199 of FIG. 1R, the vet desktop device 210 may toggle/switch between the vet's camera feed and the pet owner's camera feed with respect to making a particular camera feed larger than the other on the display shown in the UI 199.

During the video conference call with the UI 199 of FIG. 1R, the companion pet medical records 177 may be displayed to the vet on the desktop computer. Importantly, the vet may also record notes in a notes field 178 on the display device while the video call is being displayed to vet. These notes in the notes field 178 are stored by the system and then appended to the records of the off-the-shelf, vet-practice management system (V-PMS) 347 used by the clinic. Meanwhile, during the video conference, the pet owner 175 may view the video feed of the vet on the pet owner mobile device 205 in which, usually, the face of the vet 173 may be displayed, similar to what is depicted in FIG. 1R.

Referring now to FIG. 1S, this figure illustrates a user interface (UI) 201, similar to the UI 199 of FIG. 1R, that may be displayed on the vet desktop device 210 that allows a vet 173 to continue a video call with a pet mobile device 205 being operated by a pet owner 175. This UI 201 is very similar to the UI 199 of FIG. 1R so only the differences will be described here. In this UI 201, the vet desktop device 210 has switched the camera feeds relative to the UI 199 of FIG. 1R such that the camera feed of the pet owner 175 is displayed significantly larger than the camera feed for the vet 173.

Referring now to FIG. 1T, this figure illustrates a user interface (UI) 223, similar to the UI 199 of FIG. 1R, that may be displayed on the vet desktop device 210 that allows a vet 173 to end/terminate a video call with a pet mobile device 205 being operated by a pet owner 175. This UI 223 is very similar to the UI 199 of FIG. 1R so only the differences will be described here. In this UI 223, the vet desktop device 210 has ended the call such that the camera display has gone blank/black. And the vet has entered the note 187 of, "Wound looking good. Progressed as expected," in the notes field 178. The notes field 178 was also expanded in UI 223 compared to the UI 199 of FIG. 1R since text was received by the notes field 178.

Referring now to FIG. 1U, this figure illustrates a user interface (UI) 226 for the pet owner mobile device 205 such that the mobile device 205 may receive a video call from the vet desktop device 210. With this UI 226, the pet owner mobile device 205 may accept or decline a video call from the vet desktop device 210. This UI 226 may also display the name of the vet clinic which is trying to complete the video call so that the operator of the pet owner mobile device 205 will know which vet clinic has originated the video call.

Referring now to FIG. 1V, this figure illustrates a user interface (UI) 229 that may be displayed on the pet owner mobile device 205 that allows a pet owner to redeem rebates for products and/or services that were bought from the vet clinic. The UI 229 may provide for at least two options: to display rebates available for redemption (see top left of UI 229—"Available") and to display those rebates which have been submitted (see top right of UI 229—"Submitted"). In the UI 229 of FIG. 1T, the rebates "Available" for redemption option has been selected. To redeem a rebate to receive value, usually for some cash value, the user may select on on-screen button 231 labeled, "Redeem" which will send a message to the integration server 201C once pressed by the user.

Referring now to FIG. 1W, this figure illustrates a user interface (UI) 236 that may be displayed on the pet owner mobile device 205 which displays a message that the rebate selected in FIG. 1V has been sent to the vet desktop device 210 for validation. This message may also list the name of the product or service that was subject of the rebate as well as the total dollar amount for the rebate which may be rewarded once approved by the vet desktop device 210.

Referring now to FIG. 1X, this figure illustrates a user interface (UI) 239 that may be displayed on the pet owner mobile device 205 which displays an incoming message from the integration server 201C that the rebate submitted in the UI of FIG. 1W has been validated/approved by the vet desktop device 210. UI 239 is similar to UI 236 of FIG. 1W. The difference is that the UI 239 has displayed a message that was just received from the integration server 201C that the rebate from the UI 236 of FIG. 1W has been validated/approved. The pet owner mobile device 205 is instructed to select a rewards display function within the mobile application 201B so that the user may redeem the validated rebate for its value, which is usually a cash value.

However, other value schemes for rebates are possible and are included within the scope of this disclosure. Other value schemes include, but are not limited to, loyalty points (i.e. "paw points" as shown in few of the figures), discounts on future products and/or services, gift cards, and the like.

Referring now FIG. 1Y-1, this figure illustrates a user interface (UI) 239 that may be displayed on the pet owner mobile device 205 which displays a rewards function that includes rebates which have been accepted or validated by the vet desktop device 210. With this UI 239 of FIG. 1Y-1, the pet owner mobile device 205 may select a "payment method" button that is displayed adjacent to rebates that have been accepted/approved/validated by the vet desktop device 210.

Referring now FIG. 1Y-2, this figure illustrates a user interface (UI) 251 that may be displayed on the pet owner mobile device 205 which lists one or more payment options for the value of a redeemed rebate that may be selected by the pet owner mobile device 205. According to the exemplary embodiment illustrated in FIG. 1Y-2, the payment options may include, but are not limited to, Paypal™ brand of on-line accounts; Apple Wallet™ brand of on-line accounts; and a debit card account. Other payment options are possible and are included within the scope of this disclosure. Other payment options include, but are not limited to, credit cards, loyalty cards, store credit, etc.

Referring now FIG. 1Z, this figure illustrates a user interface (UI) 257 that may be displayed on the pet owner mobile device 205 which provides a message that the value of the rebate has been paid/redeemed to the financial account selected in the UI 251 of FIG. 1Y-2. The UI 257, like many of the other UIs described previously, may further display a menu bar at the bottom of the page. The menu bar may list the following commands: Home, Services, Messaging, Profile, and Rewards.

In summary for FIGS. 1V-1Z, these figures illustrate exemplary screen displays for a display device of a portable computing device (PCD) 205 in which a pet owner decides to redeem a rebate for pet products and/or services that were previously purchased from the vet of the vet clinic. The rebates are electronically redeemed when the pet owner selects each rebate for redemption. In addition to electronically deeming the rebates, the value from the rebates may be deposited electronically into a financial account of the pet owner's choosing as illustrated in FIG. Y-2.

It is noted that the rebate flow/sequence of messages illustrated in FIGS. 1V-1Z are provided as yet, one exemplary embodiment of the invention. According to other exemplary embodiments, and depending on the third party coupon/rebate provider/vendor, some of the steps or flow of the rebate process could change and/or be eliminated. For example, some third party coupon/rebate providers may not support the function of allowing the pet owner to choose which account a value from the rebate may be deposited such as illustrated in FIG. 1Y-2. Thus, according to other exemplary embodiments, FIG. 1Y-2 may be eliminated or not supported by the system.

Referring now to FIG. 2A, this figure illustrates the steps for routine 105 of method 100 illustrated in FIG. 1B in which a data connection is created between the vet desktop device 210, the integration server 201C, and the third party V-PMS 347. The first step of routine 105 is step 305 in which the integration server 201C may receive a request by a vet desktop device 210 to create an account for a vet clinic with the integration server 201C. A user interface which could be displayed for this step 305 is a typical login screen where a user may create a login-name and password as understood by one of ordinary skill in the art.

Figure 3:
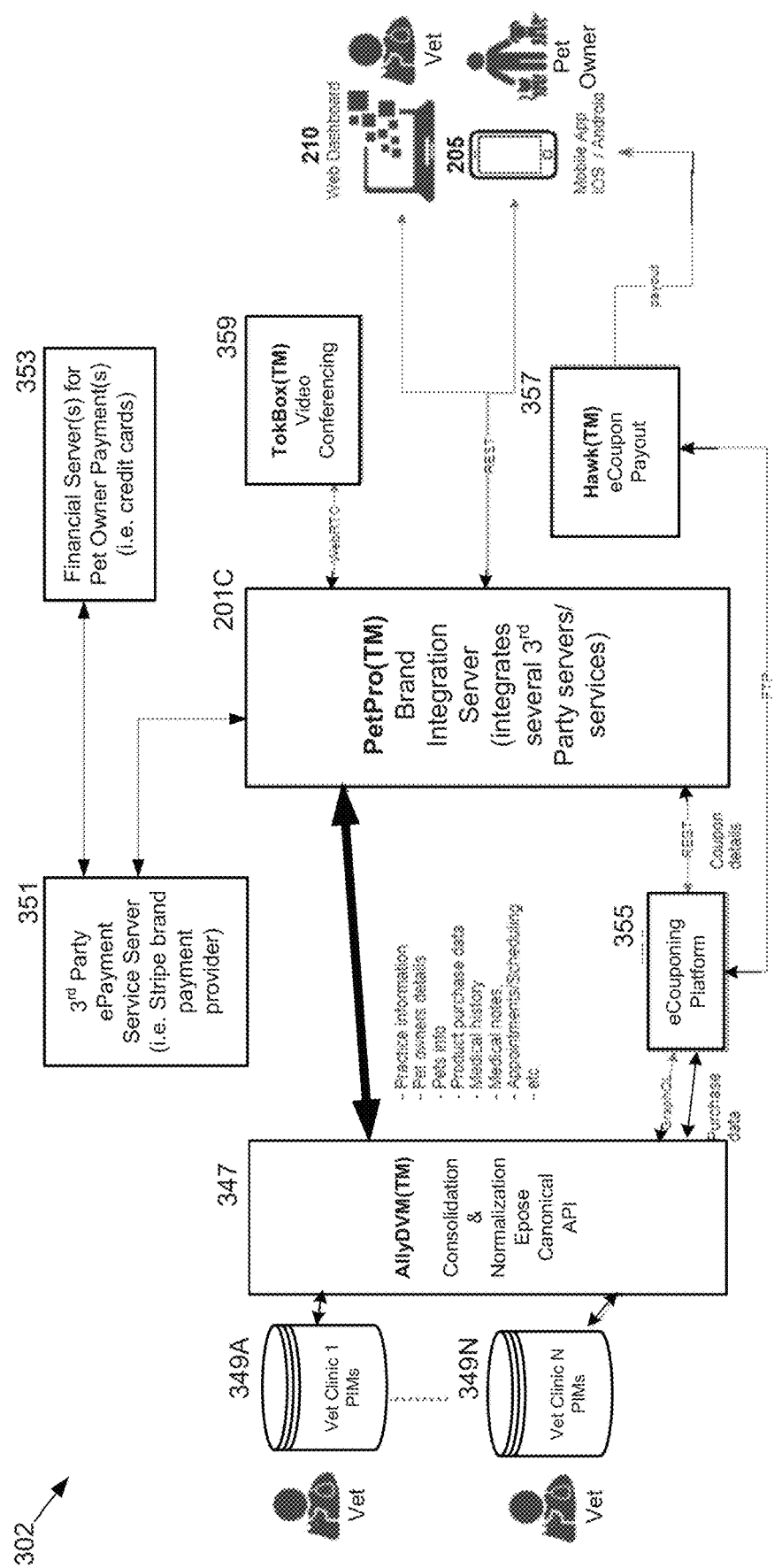
FIG. 3 illustrates a high level computer architecture for the PetPro™ brand integration server.

Next, in step 310, the integration server 201C may receive data from the desktop device 201C for creating a link between the integration server 201C and a third party vet-practice management software/service (V-PMS, software-as-as-service—SAAS) 347 [See FIG. 3]. The AllyDvm™ brand integrated pet medical records module/V-PMS 347 comprises a third party database that the integration server 201C uses to fetch vet, pet owners, pets, and medical records.

According to one exemplary embodiment, the AllyDvm™ brand V-PMS 347 is sold by Ally and more information can be found at the following URL: https://www.allydvm.com/. The data requested in this step 310 may include, but is not limited to, an e-mail address the vet desktop device 210 may use to log into the V-PMS 347 [part of third party service providers 215 illustrated in FIG. 1A]. An exemplary user interface 132 of FIG. 1C may be displayed on the vet desktop device 210 to receive related accounting information, including, but not limited to, an e-mail address associated with the vet desktop device 210.

Next, in step 315, the integration server 201C may send data comprising the vet clinic associated with the third party V-PMS 347. Subsequently, in step 320, the server 201C may receive a confirmation from the vet desktop device 210 that the correct vet clinic association has been established. The server 201C may receive this confirmation via a user interface 134 as illustrated in FIG. 1J. Next, the integration server establishes a communications link between the integration server 201C and the third party V-PMS 347.

Subsequently, in step 330, the integration server 201C may now retrieve pet owner records from the V-PMS 347. Exemplary pet records include, but are not limited to, parameters such as, but not limited to, height, length, width, girth, weight, color, fertility status (i.e.—pregnant, not pregnant . . . etc.) and other physical characteristics of the animal, as well as treatments, such as vaccine data, drug treatment data, cleanings, health issues, surgeries, feeding information etc.

Next, in step 335, the integration server 201C may display a listing of names of pet owners in which to send invitation to create account with the integration server 201C as illustrated in FIG. 1E. Access to the integration server 201C is usually by invitation only. That is, according to one exemplary embodiment, a pet owner mobile device 205 may only be able to open a new account with the integration server 201C if the vet desktop device 210 had selected a pet owner mobile device 205 for receiving an invitation or alphanumeric code directly from the integration server 201C or from some other computer.

Next, in step 340, the integration server 201C may receive a selection of one or more names of pet owners in which to send an invitation to create account with integration server 201C. After step 340, in step 345, the integration server 201C may generate a unique alpha-numeric code as the invitation code and then send that code over the network 250 to the pet owner mobile device 205. Next, the routine 105 may then return to routine 110 of FIG. 1B.

Referring now to FIG. 2B, this figure illustrates the details for routine 110 of FIG. 1B in which a data connection is created between the pet owner mobile device 205, the integration server 201C, and the third party V-PMS 347. Step 405 is the first step of Routine 110 in which integration server application program (CS-app) 201B (See FIG. 1A) is transmitted over the computer network 250 from an application store on the Internet (not shown) to a pet owner mobile device 205. This CS-app 201B allows a pet owner mobile device 205 to communicate with the integration server 201C.

Next, in step 410, the integration server 201C may receive pet owner information and an invitation code from the pet owner mobile device 205 to create an account with the integration server 201C. This step 410 generally corresponds with FIG. 1F described below. In FIG. 1F, a user interface allows a pet owner mobile device 205 to enter in the invitation code that is received from the integration server 201C based on step 345 of Routine 105 illustrated in FIG. 2A described above.

Next, in step 415, the pet owner mobile device 205 sends to the integration server 201C data for creating a link between the integration server 201C and the third party V-PMS 347 (See FIG. 3). This data usually comprises the e-mail address that the pet owner mobile device 205 uses with the vet clinic for receiving electronic communications, including e-mails, from the vet clinic. It is the e-mail address that is stored in the V-PMS 347 and that is associated with the pet owner. This step 414 is very similar to step 310 of Routine 105 of FIG. 2A described above.

Subsequently, in step 420, the integration server 201C based on the e-mail address supplied by the pet owner mobile device 205 in step 415 communicates with the third party V-PMS 347 to identify the vet clinic that is associated with the pet owner. The integration server 201C sends this vet client associated with third party V-PMS 347 to the pet owner mobile device 205 for display.

In step 425, the integration server 201C receives confirmation from the pet owner mobile device 205 that the correct vet clinic association has been established. This step 425 generally corresponds with step 320 of Routine 105 of FIG. 2A. Step 425 may also provide a user interface (UI) on the pet owner mobile device 205 similar to that shown in FIG. 1J to make this vet clinic confirmation with the pet owner mobile device 205.

Next, in step 430, the integration server 201C may retrieve pet records associated with the pet owner from the third party V-PMS 347. The pet records may include all pets associated with a pet owner. That is, a pet owner may have more than one companion animal that is being cared for by the vet clinic. For example, a pet owner may own a dog and a cat which are being cared for by the same vet clinic. In this situation, the integration server 201C may retrieve pet records for both the dog and the cat being cared for by the vet clinic.

Subsequently, in step 435, the integration server 201C may review the pet records from step 430 and determine new products and/or vet services that may be relevant to each pet based on the data in each record. For example, data in a pet record may indicate that the last anti-parasitic collar (i.e. "flea-collar") purchased for the companion animal was well over one year. Such a time duration may indicate that the companion animal may be ready for another anti-parasitic collar. This anti-parasitic collar may be new product that a pet owner may be interested in and which can be purchased from the vet clinic.

Next, step 440, the integration server 201C may send the new services and/or new products available to the pet(s) for display and available for selection on the pet owner mobile device 205. This step 440 generally corresponds with FIG. 1G described in more detail below. FIG. 1G is part of the user interface (UI) for the pet owner mobile device 205 in which the pet owner may scroll through historical pet records in addition to new products/services available for purchase from the pet clinic.

After step 440, and in step 445, the pet owner mobile device 205 may display commands available to the pet owner within the integration server app 201B including a command to set up video calls with the vet desktop device 210. This step 445 generally corresponds with FIG. 1H which illustrates commands including, but not limited to, video calls, messaging the vet desktop device 210, boarding services from the vet clinic for the companion animal, and setting up future vet appointments at the vet clinic. After step 400, the routine 110 may return to routine 115 as shown in FIG. 1B Referring now to FIG. 2C, this figure illustrates the details for routine 115 of FIG. 1B in which the pet owner mobile device 205 may receive a command within the integration server app 201B for scheduling a video call with the vet of the vet clinic. Step 505 is the first step of routine 115 in which the pet owner mobile device 205 running the integration server app 201B may receive a command to schedule a video call with the vet on the vet desktop device 210.

This step 505 generally corresponds with FIG. 2C described in more detail below. FIG. 2C is part of a user interface (UI) of the integration server app 201B in which a user may select dates and times for setting up a video call with the vet. The UI of FIG. 1C further allows a pet owner mobile device 205 to further enter third party payment information to cover the expense of the video call with the vet working from the vet desktop device 210.

Next in step 510, the pet owner mobile device 205 may receive the date and time information for scheduling the video call with the vet working from the vet desktop device 210. In steps 505 and/or 510, the integration server app 201B has received calendar/scheduling data from the integration server 201C on what days and times a vet is available for video calls. Any date and times in which the vet is unavailable cannot be selected and/or entered by the pet owner into the integration server app 201B.

Subsequently, in step 515, the pet owner mobile device 205 may display time increments for video call billing and the rate per the time increments. That is, the pet owner is shown how much a vet may charge per time increment for a video call. For example, the integration server mobile app 201C may display that a particular vet charges $15.00 U.S. dollars per 10.0 minutes of a video call.

Next, in step 520, the pet owner mobile device 205 may receive ePayment account information for the requested video call. This step 520 generally corresponds with FIG. 1D which illustrates a portion of the user interface (UI) for the integration server app 201B. The UI of FIG. 1D allows a pet owner to enter financial data for a third party ePayment account for managing payment of the scheduled video call. Exemplary financial data may include, but is not limited to, a credit card account, a debit card account, and/or a bank account (i.e. a checking account). This financial data may be stored with a third party ePayment account, such as STRIPE™ brand of ePayment services known as of this writing. However, other ePayment accounts and/or providers are possible and are included within the scope of this disclosure.

The UI of FIG. 1D generally requests the financial data (i.e. credit card info) from the pet owner without disclosing which third party ePayment account is being used for the video call billing. That is, the pet owner is not advised which third party ePayment account provider will receive the financial data (i.e. credit card information) from the integration server 201C when video call payments are made with this financial data.

Next, in step 525, the pet owner mobile device 205 transmits the date, time, and ePayment account information to the integration server 201C. Subsequently, in step 530, the integration server 201C determines if the date and time information for the video call is still available for the vet, and if so, the integration server 201C will generate an acceptance message for the appointment and transmit this acceptance message to the pet owner mobile device 205.

Subsequently, in decision step 535, the pet owner mobile device 205 determines if the pet owner desires to send a text message and/or media to the vet that will be associated with the video call. Steps 535 and 540 generally correspond with FIGS. 1L-1M which illustrate portions of a user interface (UI) for the pet owner mobile device such that a pet owner may upload text and/or media (i.e. digital photographs or video) that a pet owner may want the vet to review prior to and/or during the video call.

If the inquiry to decision step 535 is negative, then the "No" branch is followed where routine 115 ends and returns back to method 100 of FIG. 1B and specifically, routine 120. If the inquiry to decision step 535 is positive, then the "Yes" branch is followed to step 540 in which the pet owner mobile device may receive text and/or media (i.e. photos, video, etc.) and transmit that information over the communications network 250 to the integration server 201C. Routine 110 ends and then returns to routine 120 of FIG. 1B.

Referring now to FIG. 2D, this figure illustrates the details for routine 120 of FIG. 1B in which the integration server 201C may receive credentials for the same third party ePayment account service that is used for the pet owner mobile device 205 to manage billing for video calls. Step 605 is the first step of routine 120 in which the integration server 201C may receive credentials from the vet desktop device 210 for the third party ePayment account to be used for managing the billing of video calls for the system 101. That is, the vet usually needs to establish an account with the third party ePayment service and enter the vet's credentials to that account in this step. The ePayment service will transfer value from a pet owner's credit card at the end of a video call to the vet's account established with this third party ePayment service.

Steps 605 and 610 generally correspond with the user interface (UI) illustrated in FIG. 1T described in further detail below. In step 610, the vet desktop device 210 via the UI of FIG. 1T may supply the time increments and rate per time increments for the video calls made by a vet. For example, a vet may set the time increment for billing a video call at 15.0 minutes and set a rate of $20.00 U.S. Dollars per that 15.0 minutes. However, other time increments and rates are possible and are included within the scope of this disclosure. The UI of FIG. 1T allows a vet via the vet desktop device 210 to adjust this data for billing video calls as frequently as desired.

After step 610, in step 615, the integration server 201C may receive the time increments and price per time increments for video calls generated by the vet desktop device 210 and store them in memory. Next, in step 620, the integration server 210 may then transmit the vet credential to the third party ePayment service for managing payments for video calls. Routine 120 then ends and returns to method 100 of FIG. 1B, and specifically, routine 125 of FIG. 1B.

Referring now to FIG. 2E, this figure illustrates further details of routine 125 of FIG. 1B in which a video call may be established between the vet desktop device 210 and pet owner mobile device 205. Step 705 is the first step of routine 125 in which the integration server 201C may send data to the vet desktop device 210 to display calendar data that includes schedule video calls with pet owners using pet owner mobile devices 205. Step 705 generally corresponds with the user interface (UI) of FIG. 1O which illustrates how calendar data may be displayed on the desktop device 210. The UI of FIG. 1O may display a monthly calendar in one section and then additional details such as a week view in another portion as well as a daily view so that a vet may see days and time slots for upcoming video calls with pet owners. The UI of FIG. 1O may also provide commands/tools (i.e. on-screen buttons) for starting a video call as well as sending a text message to a pet owner mobile device 205.

Next in step 710, in response to a messenger command and a selected pet owner, the integration server 201C may send message data received from a pet owner mobile device previously and that is associated with a scheduled video call. The integration server 201C in this step may also send one or more pet records associated with the selected pet owner for display on the vet desktop device 210. This step 710 generally corresponds with the user interface (UI) illustrated in FIG. 1P described in more detail below. This UI of FIG. 1P may display message data that may include text and/or media info (i.e. photos and/or video) created by the pet owner mobile device in step 540 of routine 115 illustrated in FIG. 2C.

Subsequently, in step 715, in response to a client view command and a selected pet owner, the integration server 201C may send full pet record(s) associated with the selected pet owner for display on the vet desktop device 210 and the integration server may receive data for filtering the pet records. Step 715 generally corresponds to the user interface (UI) of FIG. 1Q as described above. In the UI of FIG. 1Q, complete pet records retrieved by the integration server 201C from the V-PMS 347 may be displayed. The operator of the pet desktop device 210 may select from various filter parameters in order to filter the information being displayed for a particular pet record. Exemplary filter parameters include, but are not limited to, exams, practice appointments, prescriptions, reminders, vaccinations, past video calls, etc.

After step 715, in step 720, in response to a video call command, the integration server 201C may create a video communications link between the vet desktop device 210 and a pet owner mobile device 205. Step 715 generally corresponds to the user interfaces (UIs) as illustrated in FIGS. 1R-1U described above. The UIs of FIGS. 1R-1T allow the vet desktop device 210 to adjust calling views as well as allowing the vet desktop device 210 to display and to scroll through pet records.

Next, in step 725, the vet desktop device 210 may receive notes about the video call. This step 725 may generally correspond with the UI of FIG. 1T. With the UI of FIG. 1T, the vet desktop device 210 may receive video call notes generated by a vet during the video call.

In step 730, the integration server 201C may receive an end call command from either the vet desktop device 210 or the pet owner mobile device 205. This step 730 generally corresponds with the end call command displayed in the user interfaces (UIs) of FIGS. 1R-1U.

Subsequently, in step 735, the integration server 201C may save the video call notes locally and/or to the V-PMS 347. The video call notes may be appended to the pet records maintained by the V-PMS 347. The integration server 201C in step 735 may calculate the cost for the video call by multiplying the duration of the call by the rate set by the vet desktop device 210. The integration server 201C may then relay this amount to the third party ePayment service server 351 (See FIG. 3).

Next, in step 740, the third party ePayment service provider/server 351 may deduct the calculated video call cost from the pet owner credit account via financial servers 353 and transfer this value into the account associated with the vet. The ePayment service provider/server 351 may also deduct its fee for managing the video call billing from this value taken from the pet owner credit account. Routine 125 then ends and returns to method 100 of FIG. 1B, and specifically, routine 130 of FIG. 1A.

Figure 2F:
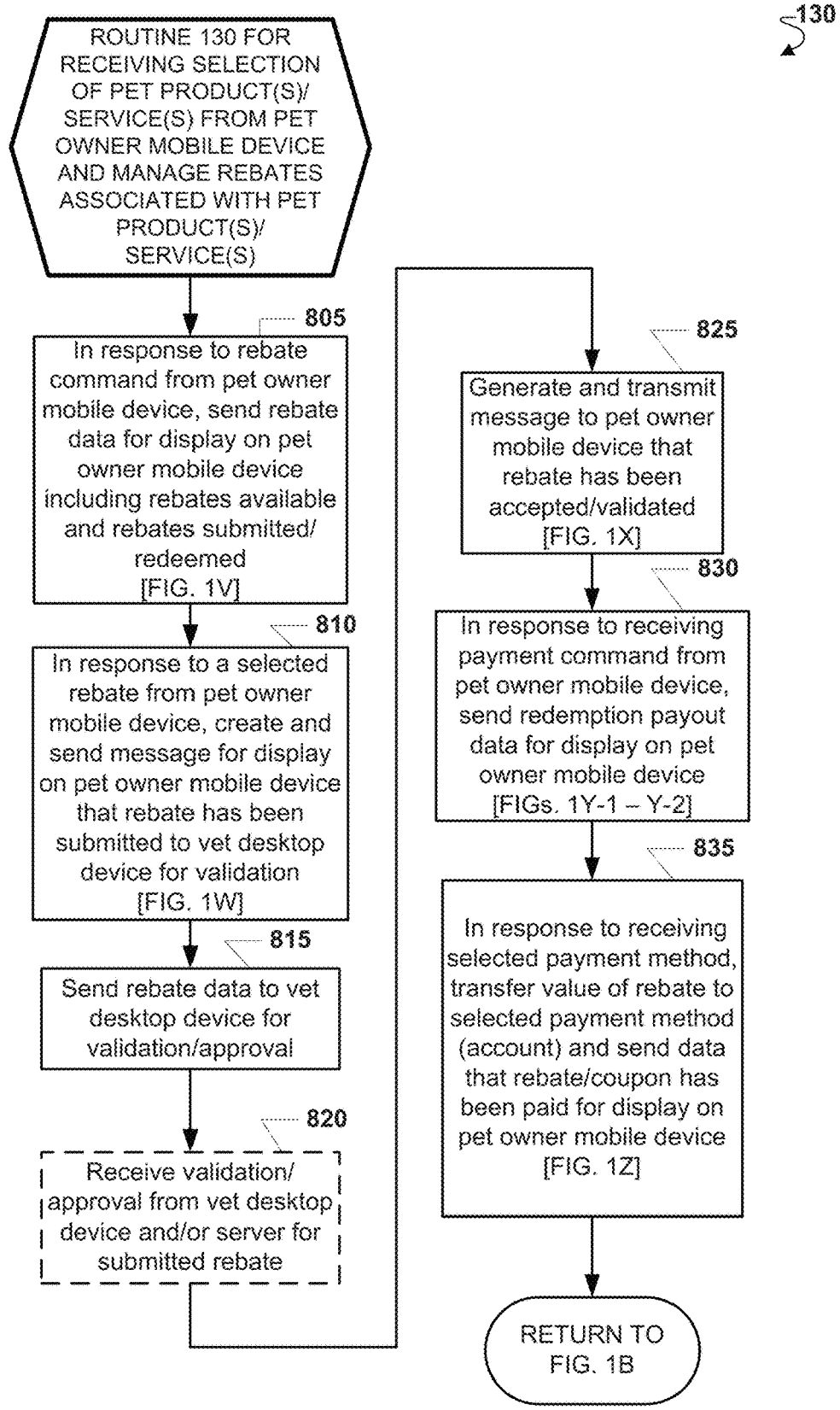
FIG. 2F illustrates the details of the sixth routine of FIG. 1A which includes receiving selection(s) of product(s)/service(s) from a pet owner mobile device and managing rebates associated with the product(s)/service(s)

Referring now to FIG. 2F, this figure illustrates the details of routine 130 of FIG. 1A which includes receiving selection(s) of product(s)/service(s) from a pet owner mobile device and managing rebates associated with the product(s)/service(s). Routine 130 generally corresponds with the user interfaces (UIs) of FIGS. 1V-1Z described above.

Step 805 is the first step of routine 130 in which the integration server 210 may send rebate data for display on the pet owner mobile device 205. The rebate data may include rebates available and rebates that have been submitted/redeemed. The rebate data may be associated with pet product(s) and/or pet service(s) sold by the vet clinic. Step 805 generally corresponds with the UI of FIG. 1V in which the pet owner may access available rebates and rebates that have been submitted/redeemed for value. The UI of FIG. 1V allows the pet owner mobile device to select rebates for product(s) and/or service(s) to be redeemed for value, such that the owner can select the cash value to be paid by one of several different payment methods as illustrated in FIG. 1Y-2 described above.

In step 810, in response to an available rebate which is selected by the pet owner mobile device 205, the integration server 201C may create and send a message for display on the pet owner mobile device 205 that a rebate has been submitted for redemption to the vet desktop device 210. This step 810 generally corresponds with the user interface (UI) of FIG. 1W. With the UI of FIG. 1W, a message is displayed on the pet owner mobile device 205 that a rebate has been submitted for acceptance/validation/approval by the vet desktop device 210. Next, in step 815, the integration server 201C may send the rebate data to the vet desktop device 210 for verification/validation/approval.

Subsequently, in step 820, the integration server 201C may receive verification/validation/approval from the vet desktop device 210 for the submitted rebate. The vet desktop device 210 may have an automated verification process (i.e., such as a set of rules) that it may follow. Alternatively, the automated verification process for rebates may occur at the integration server 201C such that a communication from the vet desktop device 210 is not needed. The integration server 201C may also have a set of rules that it can follow for its acceptance/validation/approval of a submitted rebate. Step 820 has been highlighted with dashed lines to indicate that this step may be optional and/or it may be modified such that it occurs at the server 201C and without communicating with the vet desktop device 210.

Next, in step 825, the integration server 210 may generate and transmit a message to the pet owner mobile device 205 that the rebate has been accepted/validated/approved. This step 825 generally corresponds with the user interface (UI) of FIG. 1X described above.

After step 825, in step 830, the integration server 201C may send redemption payout data for display on the pet owner mobile device 205 in response to receiving a payment command from the pet owner mobile device. This step 830 generally corresponds with the user interfaces (UIs) of FIGS. 1Y-1 & 1Y-2. In FIG. 1Y-1 & FIG. 1Y-2, the UI displays an option for a pet owner to select a payment command (FIG. 1Y-1) and then lists a plurality of options of how cash value may be sent (FIG. 1Y-2). Exemplary options include, but are not limited to, a PAYPAL™ account, an APPLE WALLET™ account, a debit card, etc. Additional and/or different payment methods are possible and are included within the scope of this disclosure.

Subsequently, in step 835, in response to receiving a selected payment method (via FIG. 1Y-2), the integration server 201C may have value transferred to the selected payment method (account) and send data such as a message that the rebate/coupon has been paid for display on the pet owner mobile device 205. This step 835 generally corresponds with the user interface (UI) of FIG. 1Z. FIG. 1Z displays that the cash value for the rebate has been transferred to the selected payment method/account from step 830 described above.

Referring now to FIG. 3, this figure illustrates a high level architecture 302 for the PetPro™ brand integration server 201C. The integration server 201C manages the services that handle all the communication between vet desktop computers 210 and pet owner PCDs 205, and it also is the device which fetches information from clinic patient/practice management system (PMS) modules 349A-349N through the third party integrated records management system module or Vet-Practice Management System (V-PMS) 347 regarding vets, pet owners, pets, medical records. One off-the-shelf V-PMS 347 sold as of this writing is the AllyDvm™ brand practice management system. With integrating the V-PMS 347 along with the other third-party components, the integration server 201C handles vet and pet owner logins, chat messaging, video calls, redeeming rebates, handling of images, push notifications for mobile devices through Google™ brand Messaging and Apple™ brand Messaging, and also is the entry point for any user request.

The AllyDvm™ brand V-PMS 347 comprises a third party database that the PetPro™ integration server 201C uses to fetch vet, pet owners, pets, and medical records. As noted previously, according to one exemplary embodiment, the AllyDvm™ brand V-PMS 347 is sold by Ally and more information can be found at the following URL: https://www.allydvm.com/.

The PMS modules 349A-349N may support the following functions: these modules 349A-349N may comprise practice manager systems that each vet clinic uses to handle user history (Pets, Pet owners, medical records). The PMS modules 349A-349N may comprise practice management servers for Veterinary clinics. PMS examples may include but are not limited to the following three websites known as of this writing:

https://vetsone.com/;
https://www.myvete.com;
https://www.animana.com.

The integration server 201C manages video calls with a third party video services module 359. A third party video services module 359 sold as of this writing is branded as TokBox™ video conferencing services: this module 359 is an external, third party existing service that the PetPro™ brand integration server 405 uses to handle video calls between the vet desktop device 210 and the pet owner mobile device 205. The integration server 201C uses one or more application programming interfaces (APIs) to communicate with the video services module 359 as understood by one of ordinary skill in the art.

Meanwhile, the eCouponing Platform module 355 coupled to the integration server 201C may support the following functions: this is another third party platform that the PetPro™ integration server 201C uses to validate that a coupon and/or rebate submitted by a pet owner is valid. In addition to the eCouponing Platform 355, an eCoupon payout module 357 may communication directly with the eCouponing Platform 355.

The eCoupon payout module 357 may comprise the HAWK™ brand e-coupon payout module 357 known as of this writing and it may work via a file transfer protocol with the eCouponing Platform 355: module 357 handles the payout to the users (Pet owners/pet owner mobile devices 205). According to one exemplary embodiment, the Hawk™ brand eCoupon module 357 is sold by Hawk Incentives, and more information can be found at the following URL: https://www.hawkincentives.com/.

The integration server 201C may be further be coupled to a third party ePayment service provider 351 for managing the billing of video calls as described above. One exemplary third party ePayment service provider known as of this writing is the STRIPE™ brand ePayment service provider owned by Stripe, Inc. However, other third party ePayment providers 351 exist and may be included with the system 101 without departing from the scope of this disclosure. The ePayment service provider 351 pulls value/credit from a financial service provider 353 and transfers this credit/value to a vet's account to allow a pet owner to pay for services and/or products purchased from the vet/vet clinic, such as video calls described above.

As illustrated in FIG. 3, the ePayment service provider 351 may be coupled to financial servers(s) 353 such as those which support credit cards, debit cards, gift cards, and other similar payment cards/accounts. The ePayment service provider 351 may process credit card based fees which may be used for the video calls between the vet desktop device 210 and the pet owner mobile device 205 as described above.

As noted previously, the integration server 201C may also manage loyalty points for payments and which also may be generated from rebates described above. See FIG. 1I described above that shows "PawPoints" in the bottom right portion of the UI 156. The integration server 201C may track a tally or total of loyalty points earned by the pet owner via rebates on certain goods/products sold by the vet. The pet owner mobile device 205 may select loyalty points, instead of credit cards, bank cards, or bank accounts, to pay for services, like video calls, and/or any products sold by the vet/vet clinic.

Figure 4:
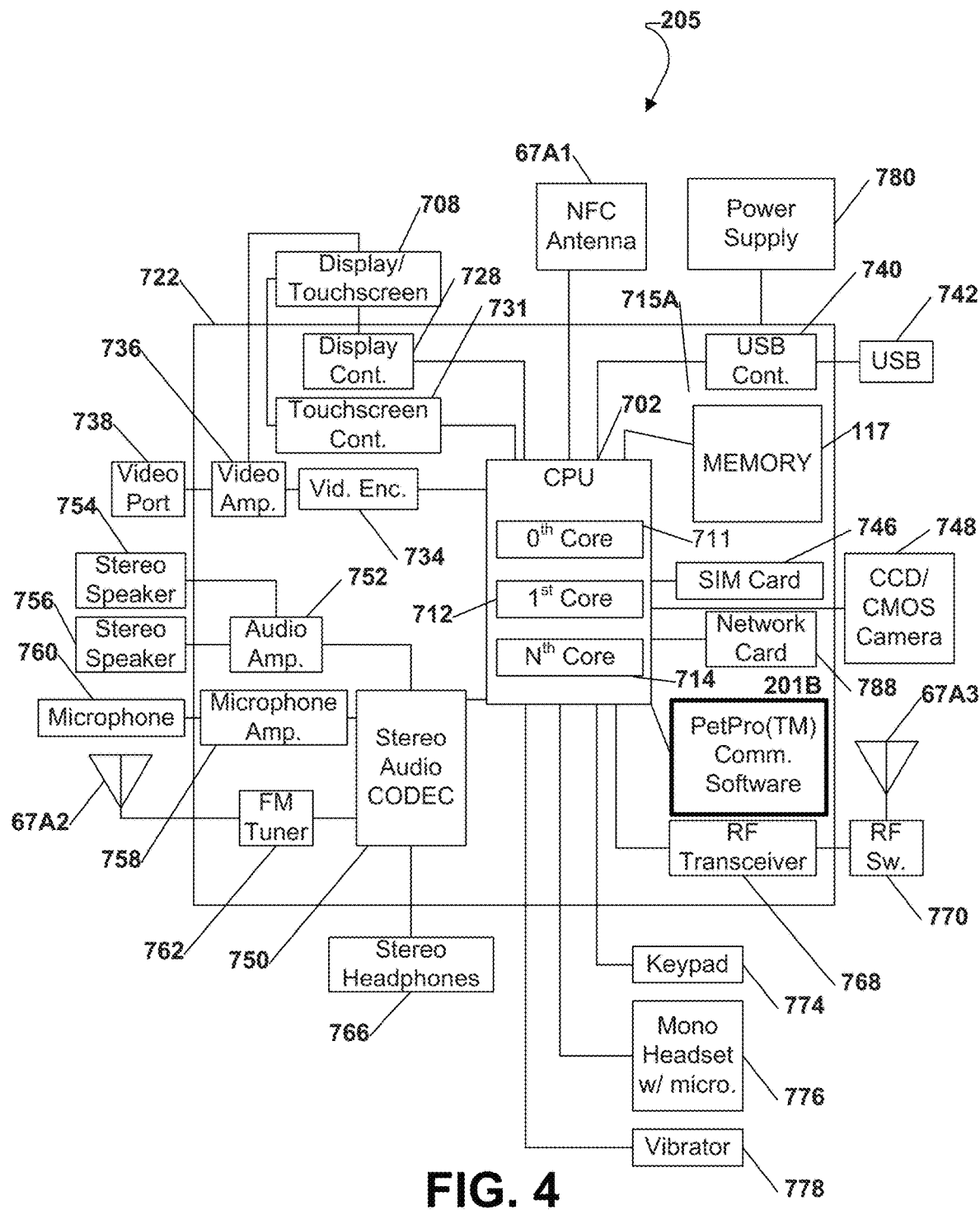
FIG. 4 illustrates one exemplary portable computing device of the system of FIG. 1A according to one exemplary embodiment of the invention.

Referring now to FIG. 4, this figure illustrates one exemplary portable computing device (PCD) 205 of the system 101 of FIG. 1A according to one exemplary embodiment of the invention. As noted above, the portable computing device (PCD) 205 may comprise a cellular telephone, a smartphone, a portable digital assistant (PDA), a portable game console, a navigation device, a tablet computer/PC, a fitness computer, and a wearable device (e.g., a sports watch, a fitness tracking device, etc.) or other battery-powered devices with a wireless connection or link. Usually, the PCD 205 is hand-held and portable: that is, it can be carried in one-hand according to a preferred, exemplary embodiment. According to one exemplary and preferred embodiment, the portable computing device 205 may comprise a hand-held, smartphone that runs a high-level operating system (HLOS).

The PCD 205 may comprise a system-on-chip (SoC) 722. The SOC 722 may include a multicore CPU 702. The multicore CPU 702 may include a zeroth core 711, a first core 712, and an Nth core 714. One of the cores may comprise, for example, a graphics processing unit (GPU) with one or more of the others comprising the CPU 702.

The multicore CPU 702 may be coupled to memory storage devices/units 117. These memory storage devices/units 117 may comprise double-data rate (DDR) dynamic random access memory (DRAM), random access memory (RAM), flash memory, and other like volatile and/or non-volatile memory types.

A second memory device may store the PetPro™ brand communications software 201B as described above in connection with FIGS. 1A-2F. The multicore CPU 702 may execute/run the communications software 201B when the CPU 702 loads it into its local memory (i.e., such as, but not limited to, flash memory) from the second storage device as understood by one of ordinary skill in the art.

A display controller 728 and a touch screen controller 731 may be coupled to the CPU 702. In turn, the touch screen display 708 external to the on-chip system 722 may be coupled to the display controller 728 and the touch screen controller 730.

FIG. 4 further shows that a video encoder 734, e.g., a phase alternating line (PAL) encoder, a sequential color a memoire (SECAM) encoder, or a national television system(s) committee (NTSC) encoder, is coupled to the multicore CPU 702. Further, a video amplifier 736 is coupled to the video encoder 734 and the touch screen display 706. Also, a video port 738 is coupled to the video amplifier 736. As shown in FIG. 7, a universal serial bus (USB) controller 740 is coupled to the multicore CPU 702. Also, a USB port 742 is coupled to the USB controller 740.

Further, as shown in FIG. 4, a digital camera 748 may be coupled to the multicore CPU 702. In an exemplary aspect, the digital camera 748 is a charge-coupled device (CCD) camera or a complementary metal-oxide semiconductor (CMOS) camera.

As further illustrated in FIG. 4, a stereo audio coder-decoder (CODEC) 750 may be coupled to the multicore CPU 702. Moreover, an audio amplifier 752 may coupled to the stereo audio CODEC 750. In an exemplary aspect, a first stereo speaker 754 and a second stereo speaker 756 are coupled to the audio amplifier 752. FIG. 4 also shows that a microphone amplifier 758 may be also coupled to the stereo audio CODEC 750.

Additionally, a microphone 760 may be coupled to the microphone amplifier 758. In a particular aspect, a frequency modulation (FM) radio tuner 762 may be coupled to the stereo audio CODEC 750. Also, an FM antenna 67A2 is coupled to the FM radio tuner 762. Further, stereo headphones 766 may be coupled to the stereo audio CODEC 750.

FIG. 4 further illustrates that a radio frequency (RF) transceiver 768 may be coupled to the multicore CPU 702. An RF switch 770 may be coupled to the RF transceiver 768 and an RF antenna 67A1. A keypad 774 may be coupled to the multicore CPU 702. Also, a mono headset with a microphone 776 may be coupled to the multicore CPU 702. Further, a vibrator device 778 may be coupled to the multicore CPU 702.

FIG. 4 also shows an NFC antenna 67A1 that may be coupled to the CPU 702. FIG. 4 further illustrates a power supply 780 coupled to the on-chip system 722. In a particular aspect, the power supply 780 is a direct current (DC) power supply that provides power to the various components of the PCD 205 that require power. Further, in a particular aspect, the power supply is a rechargeable DC battery or a DC power supply that is derived from an alternating current (AC) to DC transformer that is connected to an AC power source.

FIG. 4 further indicates that the PCD 205 may also include a network card 788 that may be used to access a data network, e.g., a local area network, a personal area network, or any other network (like 150 of FIG. 1A). The network card 788 may be a Bluetooth network card, a WiFi network card, a personal area network (PAN) card, a personal area network ultra-low-power technology (PeANUT) network card, a television/cable/satellite tuner, or any other network card well known in the art. Further, the network card 788 may be incorporated into a chip, i.e., the network card 788 may be a full solution in a chip, and may not be a separate network card 788.

As depicted in FIG. 4, the touch screen display 708, the video port 738, the USB port 742, the camera 748, the first stereo speaker 754, the second stereo speaker 756, the microphone 760, the FM antenna 764, the stereo headphones 766, the RF switch 770, the RF antenna 67A3, the NFC antenna 67A3, the keypad 774, the mono headset 776, the vibrator 778, and the power supply 780 may be external to the on-chip system 722.

Figure 5:
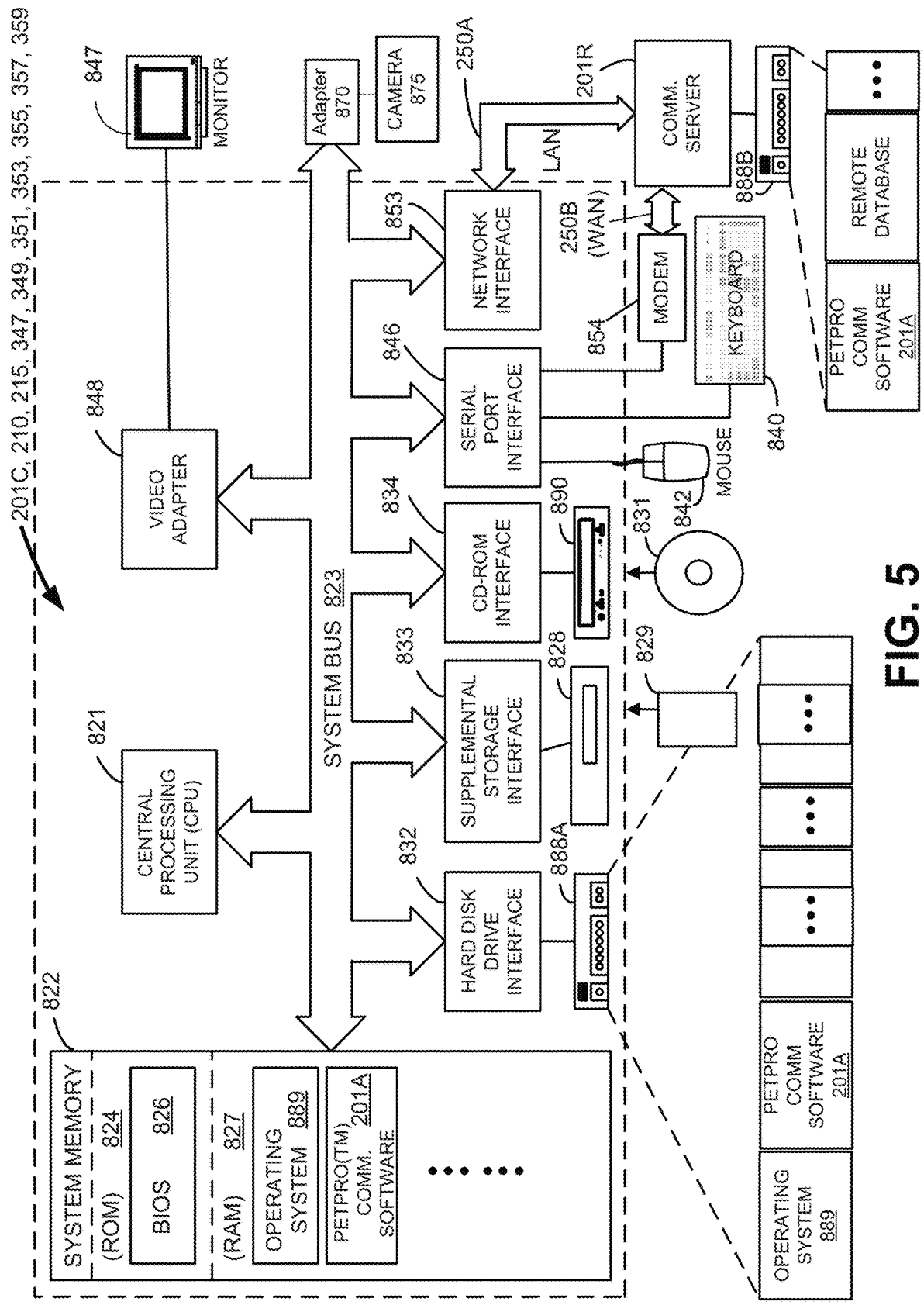
FIG. 5 is a functional block diagram of internet connected device, for example, any one of the computer servers illustrated in FIGS. 1A and 3.

Referring now to FIG. 5, this figure is a functional block diagram of internet connected device, for example, any one of the computer servers 201C, 210, 215, 347, 349, 351, 353 355, 357, 359 illustrated in FIGS. 1A and 3. The exemplary operating environment for the system 101 of FIGS. 1A and 3 includes a computing device in the form of a conventional or general purpose computer 201C, 210, 215, 347, 349, 351, 353 355, 357, 359 [hereinafter, collectively "computers 201C" ] which may be programmed as special purpose computers to perform the disclosed algorithms (shown in flow chart forms) illustrated in FIGS. 1B-2E.

Generally, a computer 201C includes a processing unit 821, a system memory 822, and a system bus 823 that couples various system components including the system memory 822 to the processing unit 821. The system bus 823 may be any of several types of bus structures including a memory bus or memory controller, a peripheral bus, and a local bus using any of a variety of bus architectures.

The system memory 822 includes a read-only memory (ROM) 824 and a random access memory (RAM) 827. A basic input/output system (BIOS) 826, containing the basic routines that help to transfer information between elements within computer 201C, such as during start-up, is stored in ROM 824.

The computer 201C can include a hard disk drive 888A for reading from and writing to a hard disk, not shown, a supplemental storage drive 833 for reading from or writing to a removable supplemental storage 829 (like flash memory and/or a USB drive) and an optical disk drive 890 for reading from or writing to a removable optical disk 831 such as a CD-ROM or other optical media. Hard disk drive 888A, supplemental storage 829, and the optical disk drive 890 are connected to system bus 823 by a hard disk drive interface 832, a supplemental storage drive interface 833, and an optical disk drive interface 834, respectively.

Although the exemplary environment described herein employs hard disk 888A, removable supplemental storage 829, and a removable optical disk 831, it should be appreciated by those skilled in the art that other types of computer readable media which can store data that is accessible by a computer, such as magnetic cassettes, flash memory cards, digital video disks, Bernoulli cartridges, RAMs, ROMs, and the like, may also be used in the exemplary operating environment without departing from the scope of this disclosure. Such uses of other forms of computer readable media besides the hardware illustrated will be used in internet connected devices such as in the servers 201C and mobile phone 205 of system 101 of FIG. 1A.

The drives and their associated computer readable media illustrated in FIG. 5 provide nonvolatile storage of computer-executable instructions, data structures, program modules, and other data for computer or client device, like a mobile phone 205 of FIG. 4. A number of program modules may be stored on hard disk 888, supplemental storage 829, optical disk 831, ROM 824, or RAM 827, including, but not limited to, an operating system (OS) 889 and the PetPro™ brand communications software 201A. Program modules include routines, sub-routines, programs, objects, components, data structures, etc., which perform particular tasks or implement particular abstract data types. Aspects of the present invention may be implemented in the form of a downloadable, client-side, PetPro™ communications software application 201B which is executed by the phone 205 in system 101 of FIG. 1A.

A user may enter commands and information into computer 201C through input devices, such as a keyboard 840 and a pointing device 842. Pointing devices may include a mouse, a trackball, and an electronic pen that can be used in conjunction with an electronic tablet. Other input devices (not shown) may include a microphone, joystick, game pad, satellite dish, scanner, or the like. These and other input devices are often connected to processing unit 821 through a serial port interface 846 that is coupled to the system bus 823, but may be connected by other interfaces, such as a parallel port, game port, a universal serial bus (USB), or the like.

The display 847 may also be connected to system bus 823 via an interface, such as a video adapter 848. As noted above, the display 847 can comprise any type of display devices such as a liquid crystal display (LCD), a plasma display, an organic light-emitting diode (OLED) display, and a cathode ray tube (CRT) display.

The camera 875 may also be connected to system bus 823 via an interface, such as an adapter 870. As noted previously, the camera 875 can comprise a video camera such as a webcam. The camera 875 can be a CCD (charge-coupled device) camera or a CMOS (complementary metal-oxide-semiconductor) camera. In addition to the monitor 847 and camera 875, server 210, comprising a computer, may include other peripheral output devices (not shown), such as speakers and printers.

The computer 201C may operate in a networked environment using logical connections to one or more remote computers, such as another server 201R of FIG. 5. A remote computer 201R may take the form as another personal computer, a server, a mobile phone, a router, a networked PC, a peer device, or other common network node. While a server or a remote computer 201R typically includes many or all of the elements described above, only a memory storage device 888B has been illustrated FIG. 5.

The logical connections depicted in FIG. 5 include a local area network (LAN) 250A and a wide area network (WAN) 250A. Such networking environments are commonplace in offices, enterprise-wide computer networks, intranets, and the Internet. Communication networks 250 of FIG. 5 correspond with the communication network 250 illustrated with FIG. 1A.

When used in a LAN networking environment 250A, the computer 201C is often connected to the local area network 250A through a network interface or adapter 853. When used in a WAN networking environment, the computer 210 typically includes a modem 854 or other means for establishing communications over WAN 250B, such as the Internet. Modem 854, which may be internal or external, is connected to system bus 823 via serial port interface 846. In a networked environment, program modules depicted relative to the server 201C, or portions thereof, may be stored in the remote memory storage device 888B of the remote computer 201R, and vice-versa. It will be appreciated that the network connections shown are exemplary and other means of establishing a communications link between the computers 201C, 201R and mobile phones 205 of FIG. 1A may be used.

Moreover, those skilled in the art will appreciate that the present system 101 of FIG. 1A which employs computers 201C, 210 may be implemented in other computer system configurations, including hand-held devices—like mobile phone 205 of FIG. 4, multiprocessor systems, microprocessor based or programmable consumer electronics, network personal computers, minicomputers, mainframe computers, and the like. The system 101 of FIG. 1A may also be practiced in distributed computing environments, where tasks are performed by remote processing devices that are linked through the communications network 250. In a distributed computing environment, program modules may be located in both local and remote memory storage devices.

Certain steps in the processes or process flows described in this specification naturally precede others for the invention to function as described. However, the invention is not limited to the order of the steps described if such order or sequence does not alter the functionality of the invention. That is, it is recognized that some steps may be performed before, after, or parallel (substantially simultaneously with) other steps without departing from the scope and spirit of the invention. Further, words such and "thereafter", "then", "next", etc. are not intended to limit the order of the steps. These words are simply used to guide the reader through the description of the exemplary method.

Exemplary Off-the-Shelf 3$^{rd}$ Party Products & Implementations

The integration server 201C (which may also comprise a plurality of servers 201C) may be managed by OpenShift™ brand software. Openshift™ software is a family of containerization software developed by Red Hat™ corporation, known as of this writing. The OpenShift™ Container Platform may comprise an on-premises platform as a service built around docker containers orchestrated and managed by kubernetes on a foundation of Red Hat™ Enterprise Linux.

A PetPro™ brand database may be coupled to the integration server 201C and/or may be part of the integration server 201C. This database comprise a sequential query language (SQL) database. Exemplary vendors for database services that form this database may include Amazon™ brand web services (AWS) known as of this writing. The PetPro™ brand integration servers 201C may communicate with various third party servers.

The communications software 201 of the Pet Owner software may include a Fe-module used by pet owners for Android and IOS (Apple). It was developed in Angular 6 and Ionic known as of this writing: see more information at the URL—https://ionicframework.com/.

The communications software 210 for the vet desktop application may comprise a Fe-angular module: this is a web app used by vets for internet web browsers. It was develop by angular 6 known as of this writing.

The integration server 201C may communicate with Google Messaging and Apple Messaging server. This server 201C stores device identifiers of mobile devices [i.e. phones] by user id, in order to identify who is the message for and send it.

A portion of the integration server 201C may comprise a Be-spring-boot server: which is the server 201C who handles the greater part of entry points for the users, Appointment creation, user creation, clinic creation, fetch information for pets, pet owners, vets, medical records, payment information, etc. The Integration server 201C communicates with the Opentok™ brand server 359 (See FIG. 3) [a third party server/service for establishing video conferencing] as well as the AllyDVM™ brand server 415 [a third party server/service discussed above for animal medical records].

The Be-PetPro™ brand-chat integration server 201C: is the server in charge to create chat sessions between users [i.e. vets on desktop computers 210 and pet owners on mobile devices 205 like phones], and then send messages between them.

The integration server 201C may use and/or comprise a Be-file-server: this is a server 201C who handle all the images, it use a drive to store these files in a storage volume, also expose endpoints directly to the users to save and get files. The storage volume of the integration server 201C may also use OpenShift software as described above.

The integration server 201C may include or code for a Be-rebate-server: This server communicates with the eCoupon Platform 355 [third party server/services] and a Hawk server [third party server/services] for the coupon validation process and expose endpoints for the user to fetch rebates and their status.

The integration server 201C may comprise Amazon Web Services (AWS)™ Relational Database Service (RDS): it comprise three (3) databases: one RDS may be used by the spring-boot server to store everything related to Vets (Service provider), pet owners, pets, chats, videos, payment, appointment, and also the relationship with our external partner AllyDvm.

Another portion of the integration server 201C may include a new array that may be used by the rebate server 357 to store coupons definitions and the status of already redeemed coupons.

The integration server 201C may work with Apple and Google severs. The integration server 201C may communicate with third party messaging systems, video conferencing providers, pet record management providers, and eCoupon/eRebate providers, and practice management systems (PMS) mentioned above form, yet one exemplary embodiment of the invention. Other providers with different services/functions may be employed without departing from this disclosure.

Additionally, one of ordinary skill in programming is able to write computer code or identify appropriate hardware and/or circuits to implement the disclosed invention without difficulty based on the flow charts and associated description in this specification.

Therefore, disclosure of a particular set of program code instructions or detailed hardware devices is not considered necessary for an adequate understanding of how to make and use the invention. The inventive functionality of the claimed computer implemented process is explained in more detail in the above description and in conjunction with the figures that may illustrate various processes flows.

In one or more exemplary aspects, the functions described may be implemented in hardware, software, firmware, or any combination thereof. If implemented in software, the functions may be stored on or transmitted as one or more instructions or code on a computer-readable medium. Computer-readable media include both storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM, Flash, or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, Server, or other remote source, such as in "cloud" computing, using a coaxial cable, fiber optic cable, twisted pair, digital subscriber line ("DSL"), or wireless technologies such as infrared, radio, and microwave, then the coaxial cable, fiber optic cable, twisted pair, DSL, or wireless technologies such as infrared, radio, and microwave are included in the definition of medium.

Disk and disc, as used herein, includes compact disc ("CD"), laser disc, optical disc, digital versatile disc ("DVD"), floppy disk, and blue-ray disc where disks usually reproduce data magnetically, while discs reproduce data optically with lasers. Combinations of the above should also be included within the scope or computer-readable media.

Alternative embodiments for the system and method of the present disclosure will become apparent to one of ordinary skill in the art to which the invention pertains without departing from its spirit and scope. Therefore, although selected aspects have been illustrated and described in detail, it will be understood that various substitutions and alterations may be made therein without departing from the spirit and scope of the present invention, as defined by the following claims.

What is claimed is:

1. A computer-implemented method for integrating communications between a veterinarian, service providers, and a pet owner comprising:
   sending a message from an integration server requesting a payment account, the payment account being charged for one or more services rendered by the veterinarian;
   sending a message from the integration server providing calendar data; the calendar data listing days and time slots in which the veterinarian is available for a video conference;
   receiving a selection of a day and time slot in which the veterinarian was listed as available for a video conference;
   the integration server receiving from a communications network a message containing information about the payment account;
   verifying with the integration server that the payment account contains sufficient funds for the requested video conference;
   transmitting a confirmation message from the integration server over the communications network, the confirmation message indicating that the selected time slot and day have been reserved with the veterinarian for a video conference;
   receiving a text message with the integration server from a portable computing device for the veterinarian, the text message comprising a photograph;
   displaying the photograph from the text message on a display screen of computer within a clinic;
   sending a request to initiate the video conference, the request originating from the computer within the clinic for establishing a video conference between the computer within the clinic and the portable computing device;
   displaying on the display screen of the computer within the clinic pet medical records simultaneously with video from the video conference;
   receiving note data with the computer within the clinic; and
   displaying the note data simultaneously with the pet medical records and video from the video conference on the display screen of the computer within the clinic.

2. The method of claim 1, further comprising: receiving with the server a request from the communications network for redeeming an electronic rebate.

3. The method of claim 2, further comprising: completing a redemption of the electronic rebate, the redemption comprising a value of currency.

4. The method of claim 3, further comprising: sending a redemption message over the communications network, the redemption message indicating that validation of the rebate has been completed.

5. The method of claim 4, further comprising: sending a payment message over the communications network, the payment message requesting an identity of a payment account within which to deposit the value of currency generated from the validation of the rebate.

6. A system for managing communications between a veterinarian and a pet owner comprising:
   means for providing a payment account with a portable computing device, the payment account to be charged for one or more future services rendered by the veterinarian;

means for accessing calendar data in a database with a portable computing device; the calendar data listing days on which the veterinarian is available for a video conference;

means for selecting a day on which the veterinarian is available for a video conference with the portable computing device;

means for displaying on the portable computing device time slots within the selected day in which the veterinarian is available for a video conference with the portable computing device;

means for selecting with the portable computing device a time slot for a video conference with the veterinarian;

means for transmitting the selected time slot over a communications network to the database;

means for receiving a first message from the communications network with the portable computing device, the first message requesting a payment account verification;

means for sending a second message over the communications network from the portable computing device, the second message containing information about the payment account;

means for verifying that the payment account contains sufficient funds for the requested video conference; and means for transmitting a third message over the communications network to the portable computing device, the third message confirming that the selected time slot within the selected day has been reserved with the veterinarian for a video conference;

means for receiving a text message from a portable computing device for the veterinarian, the text message comprising a photograph;

means for displaying the photograph from the text message on a display screen of computer within a clinic;

means for sending a request to initiate the video conference, the request originating from the computer within the clinic for establishing a video conference between the computer within the clinic and the portable computing device;

means for displaying on the display screen of the computer within the clinic pet medical records simultaneously with video from the video conference;

means for receiving note data with the computer within the clinic; and means for displaying the note data simultaneously with the pet medical records and video from the video conference on the display screen of the computer within the clinic.

7. The system of claim 6, further comprising: means for receiving a request from the portable computing device for redeeming an electronic rebate.

8. The system of claim 7, further comprising: means for completing a redemption of the electronic rebate, the redemption comprising a value of currency.

9. The system of claim 8, further comprising: means for sending a fourth message to the portable computing device over the communications network, the fourth message indicating that the redemption of the rebate has been completed.

10. The system of claim 4, further comprising: means for sending a fifth message to the portable computing device over the communications network, the fifth message requesting an identity of a payment account within which to deposit the value of currency generated from the redemption of the rebate.

* * * * *